(12) United States Patent
Chopra

(10) Patent No.: US 12,310,675 B2
(45) Date of Patent: *May 27, 2025

(54) SYSTEMS AND METHODS FOR DEVICE-AWARE FLEXIBLE TOOL REGISTRATION

(71) Applicant: INTUITIVE SURGICAL OPERATIONS, INC., Sunnyvale, CA (US)

(72) Inventor: Prashant Chopra, Foster City, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 347 days.

This patent is subject to a terminal disclaimer.

(21) Appl. No.: 17/890,995

(22) Filed: Aug. 18, 2022

(65) Prior Publication Data

US 2023/0046239 A1 Feb. 16, 2023

Related U.S. Application Data

(63) Continuation of application No. 16/815,328, filed on Mar. 11, 2020, now Pat. No. 11,452,569, which is a
(Continued)

(51) Int. Cl.
*A61B 34/20* (2016.01)
*A61B 1/267* (2006.01)
(Continued)

(52) U.S. Cl.
CPC ............ *A61B 34/20* (2016.02); *A61B 1/267* (2013.01); *A61B 1/2676* (2013.01); *A61B 5/062* (2013.01);
(Continued)

(58) Field of Classification Search
CPC ....... A61B 34/20; A61B 1/267; A61B 1/2676; A61B 5/062; A61B 5/066; A61B 5/08;
(Continued)

(56) References Cited

U.S. PATENT DOCUMENTS 6,380,732 B1 4/2002 Gilboa
6,389,187 B1 5/2002 Greenaway et al.
(Continued)

FOREIGN PATENT DOCUMENTS

EP 2774528 A1 9/2014
JP H03177682 A 8/1991
(Continued)

OTHER PUBLICATIONS

Extended European Search Report for Application No. 14870214.5, mailed on Jul. 5, 2017, 10 pages.
(Continued)

*Primary Examiner* — Joel Lamprecht
(74) *Attorney, Agent, or Firm* — Haynes & Boone, LLP.

(57) ABSTRACT

A medical system comprises a flexible device configured to be positioned at least partially within an anatomical passageway of a plurality of anatomical passageways within a patient anatomy. The medical system further comprises a memory device including computer executable instructions. The computer executable instructions are for performing operations comprising determining a deformation force exerted by a section of the flexible device. The operations further comprise registering a model of a candidate anatomical passageway of the plurality of anatomical passageways to a model of the flexible device based on: a shape of the flexible device; and the deformation force exerted by the section of the flexible device.

20 Claims, 21 Drawing Sheets

Related U.S. Application Data continuation of application No. 15/101,518, filed as application No. PCT/US2014/069228 on Dec. 9, 2014, now Pat. No. 10,610,306.

(60) Provisional application No. 61/913,747, filed on Dec. 9, 2013.

(51) Int. Cl.

| | | |
|---|---|---|
| *A61B 5/00* | (2006.01) | |
| *A61B 5/06* | (2006.01) | |
| *A61B 5/08* | (2006.01) | |
| *A61B 34/30* | (2016.01) | |
| *A61B 34/35* | (2016.01) | |
| *A61B 34/37* | (2016.01) | |
| *G16H 50/50* | (2018.01) | |
| *A61B 17/00* | (2006.01) | |
| *A61B 18/14* | (2006.01) | |
| *A61B 34/00* | (2016.01) | |
| *A61B 34/10* | (2016.01) | |
| *A61B 90/00* | (2016.01) | |
| *A61M 25/01* | (2006.01) | |

(52) U.S. Cl.
CPC ............... *A61B 5/066* (2013.01); *A61B 5/08* (2013.01); *A61B 5/6852* (2013.01); *A61B 34/30* (2016.02); *A61B 34/35* (2016.02); *A61B 34/37* (2016.02); *G16H 50/50* (2018.01); *A61B 2017/00203* (2013.01); *A61B 2017/00323* (2013.01); *A61B 2017/00809* (2013.01); *A61B 18/1492* (2013.01); *A61B 2034/104* (2016.02); *A61B 2034/105* (2016.02); *A61B 2034/2051* (2016.02); *A61B 2034/2061* (2016.02); *A61B 2034/301* (2016.02); *A61B 2034/306* (2016.02); *A61B 2034/741* (2016.02); *A61B 2034/742* (2016.02); *A61B 2090/064* (2016.02); *A61B 2090/065* (2016.02); *A61M 2025/0166* (2013.01)

(58) Field of Classification Search
CPC ....... A61B 5/6852; A61B 34/30; A61B 34/35; A61B 34/37; A61B 18/1492; A61B 2017/00203; A61B 2017/00323; A61B 2017/00809; A61B 2034/104; A61B 2034/105; A61B 2034/2051; A61B 2034/2061; A61B 2034/301; A61B 2034/306; A61B 2034/741; A61B 2034/742; A61B 2090/064; A61B 2090/065; A61B 1/009; A61B 34/00; A61B 90/39; A61B 2017/003; G16H 50/50; A61M 2025/0166

See application file for complete search history.

(56) References Cited

U.S. PATENT DOCUMENTS

| | | | |
|---|---|---|---|
| 7,772,541 B2 | 8/2010 | Froggatt et al. | |
| 7,781,724 B2 | 8/2010 | Childers et al. | |
| 7,930,065 B2 | 4/2011 | Larkin et al. | |
| 8,900,131 B2 | 12/2014 | Chopra et al. | |
| 10,085,671 B2 | 10/2018 | Duindam et al. | |
| 10,610,306 B2 * | 4/2020 | Chopra | A61B 5/062 |
| 11,452,569 B2 * | 9/2022 | Chopra | A61B 34/30 |
| 2006/0013523 A1 | 1/2006 | Childers et al. | |
| 2011/0270082 A1 | 11/2011 | Turner et al. | |
| 2011/0319714 A1 | 12/2011 | Roelle et al. | |
| 2011/0319910 A1 | 12/2011 | Roelle et al. | |
| 2012/0017923 A1 | 1/2012 | Sobe | |
| 2012/0247192 A1 | 10/2012 | Diaz et al. | |
| 2012/0289843 A1 | 11/2012 | Chopra et al. | |
| 2020/0205904 A1 | 7/2020 | Chopra | |

FOREIGN PATENT DOCUMENTS

| | | |
|---|---|---|
| JP | H06509971 A | 11/1994 |
| JP | 2000083889 A | 3/2000 |
| JP | 2005505355 A | 2/2005 |
| JP | 2011206251 A | 10/2011 |
| WO | WO-2007141784 A2 | 12/2007 |
| WO | WO-2011102012 A1 | 8/2011 |
| WO | WO-2012158324 A2 | 11/2012 |
| WO | WO-2013065606 A1 | 5/2013 |
| WO | WO-2013173229 A1 | 11/2013 |

OTHER PUBLICATIONS

International Preliminary Report on Patentability for Application No. PCT/US2014/069228, mailed on Jun. 23, 2016, 10 pages.
International Search Report and Written Opinion for Application No. PCT/US14/69228, mailed on Mar. 13, 2015, 13 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
"Springer Handbook of Robotics," Bruno Siciliano & Oussama Khatib (Editors), Kinematics, Springer, 2008, pp. 27-29.

* cited by examiner ically invasive instrument to the anatomical system is a time consuming and processing intensive task. Improved systems and methods are needed for increasing the accuracy and efficiency of systems and methods of registering minimally invasive instruments to the anatomical system.

SYSTEMS AND METHODS FOR DEVICE-AWARE FLEXIBLE TOOL REGISTRATION

CROSS-REFERENCE TO RELATED APPLICATIONS

This application is a continuation of U.S. patent application Ser. No. 16/815,328, filed Mar. 11, 2020, which is a continuation of U.S. patent application Ser. No. 15/101,518, filed Jun. 3, 2016, now U.S. Pat. No. 10,610,306, which is the U.S. National Phase of International Patent Application No. PCT/US2014/069228, filed Dec. 9, 2014, which designated the U.S. and claims priority to and the benefit of U.S. Provisional Patent Application No. 61/913,747, filed Dec. 9, 2013, entitled "Systems and Methods for Device-Aware Flexible Tool Registration," all of which are incorporated by reference herein in their entireties.

FIELD

The present disclosure is directed to systems and methods for tracking a medical device within a patient anatomy during a medical procedure, and more particularly to systems and methods for efficiently tracking a medical device within a patient anatomy using a shape sensor and/or a position sensor.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Clinicians may insert medical tool through these natural orifices or incisions to reach a target tissue location. Medical tools include instruments such as therapeutic instruments, diagnostic instruments, and surgical instruments. To reach the target tissue location, a minimally invasive medical tool may navigate natural or surgically created passageways in anatomical systems such as the lungs, the colon, the intestines, the kidneys, the heart, the circulatory system, or the like.

Minimally invasive surgical procedures typically rely on some sort of instrument position monitoring to ensure proper access to, and behavior at, the target tissue location. Conventional minimally invasive surgical instruments are generally either formed from generally rigid, elongate elements (e.g., laparoscopic or teleoperational systems) or highly flexible systems designed to follow a predetermined anatomic path (e.g., angioplasty balloon catheters). in either case, position monitoring typically involves localized tracking of a discrete portion of the instrument (e.g., the distal tip of a catheter). The remaining guidewire/catheter length is not actively monitored, except in an incidental sense to the extent the remaining length is shown during fluoroscopic visualization of the tip advancement.

However, increasingly more complex minimally invasive surgical systems can require enhanced instrument position monitoring for safe and effective use. Navigational assist systems help the clinician route the surgical instruments and avoid damage to the anatomy. These systems can incorporate the use of shape sensors to more accurately describe the shape, pose, and location of the surgical instrument in real space or with respect to pre-procedural or concurrent images. In a dynamic anatomical system and/or in an anatomical region dense with many anatomical passageways, accurately registering the minimally invasive instrument to the anatomical system is a time consuming and processing intensive task. Improved systems and methods are needed for increasing the accuracy and efficiency of systems and methods of registering minimally invasive instruments to the anatomical system.

SUMMARY

In one aspect, the present disclosure describes a method of determining the accurate positioning of a device within a patient anatomy. The method comprises generating a first model of at least one anatomical passageway from anatomical data describing the patient anatomy. In one aspect, the method comprises determining a shape of a device positioned within branched anatomical passageways of the patient anatomy, the device including a plurality of sections, each section of the plurality of sections having a distinct physical property, and computing a set of deformation forces for each section of the plurality of sections of the device. In one aspect, the method comprises generating a second model of the device positioned within the plurality of branched anatomical passageways by adjusting the first model based upon the determined shape of the device and the set of deformation forces for each section of the plurality of sections of the device.

In another aspect. the present disclosure describes a medical system comprising a flexible device including a shape sensor, a memory, and a non-transitory computer readable media. In one aspect, the memory can store anatomical data describing a patient anatomy, and the non-transitory computer readable media can contain computer executable instructions for registering the flexible device to the anatomical data describing the patient anatomy. In one aspect, the computer executable instructions include instructions for generating a first model of a plurality of branched anatomical passageways from the stored anatomical data describing the patient anatomy, instructions for receiving information from the shape sensor to determine a shape of the device positioned within the plurality of branched anatomical passageways, the device including a plurality of sections, each section of the plurality of sections having a distinct physical property, instructions for computing a set of deformation forces for each section of the plurality of different sections of the device, and/or instructions for generating a second model of the device positioned within the plurality of branched anatomical passageways by adjusting the first model based upon the determined shape of the device and the set of deformation forces for each section of the plurality of sections of the device.

BRIEF DESCRIPTIONS OF THE DRAWINGS

Aspects of the present disclosure arc best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 12:
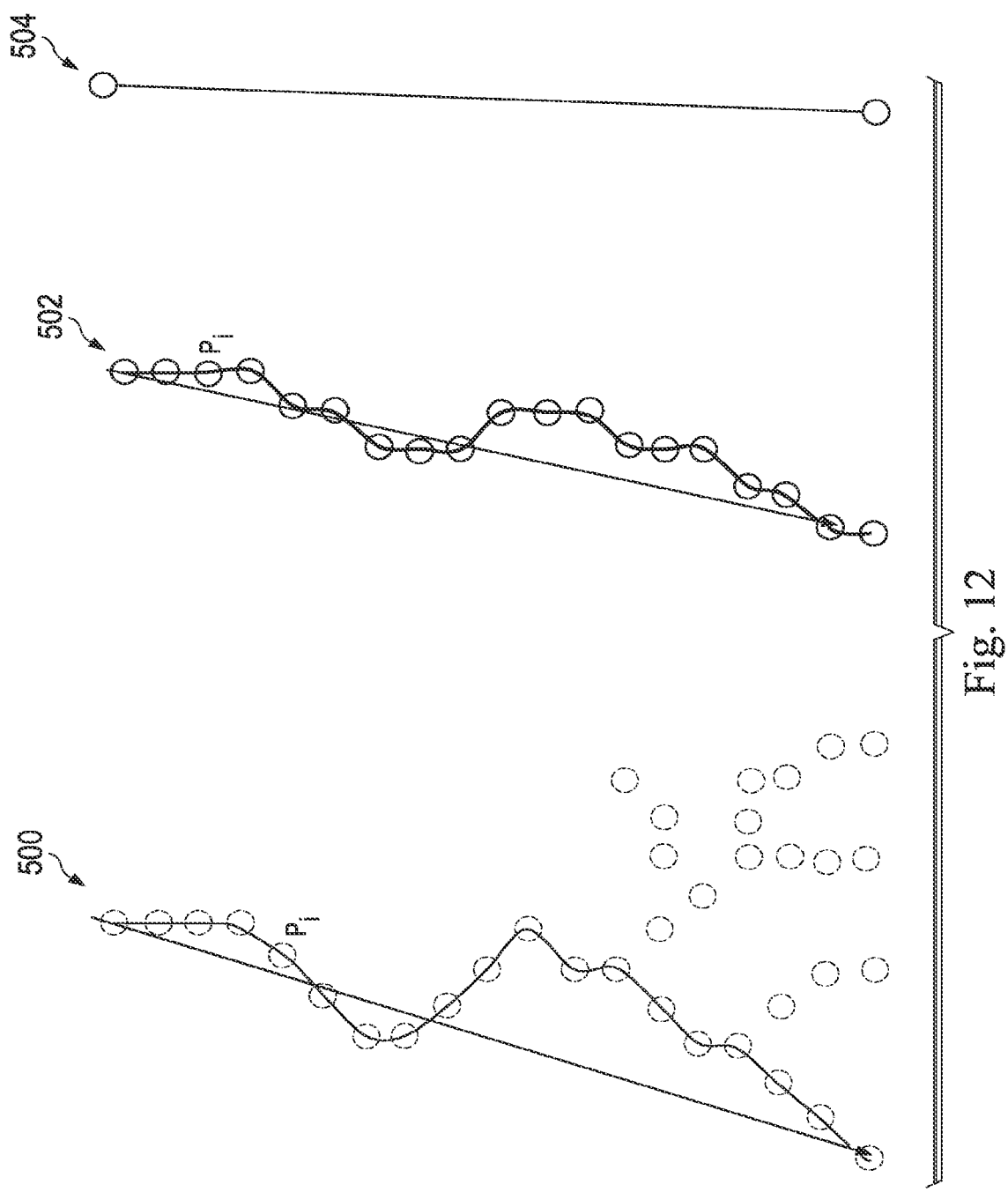

FIG. 12 includes illustrations of models of an anatomical passageway according to another embodiment of the disclosure.

Figure 13:
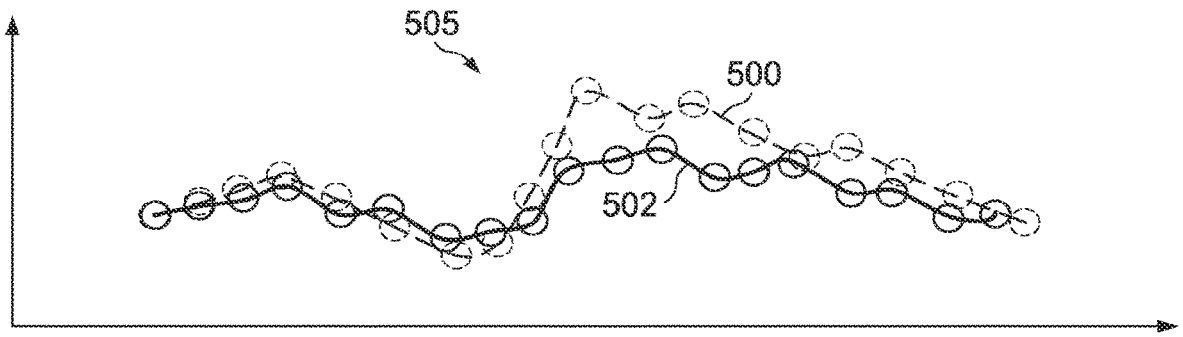

FIG. 13 is a histogram for matching the model of FIG. 12.

Figure 14:
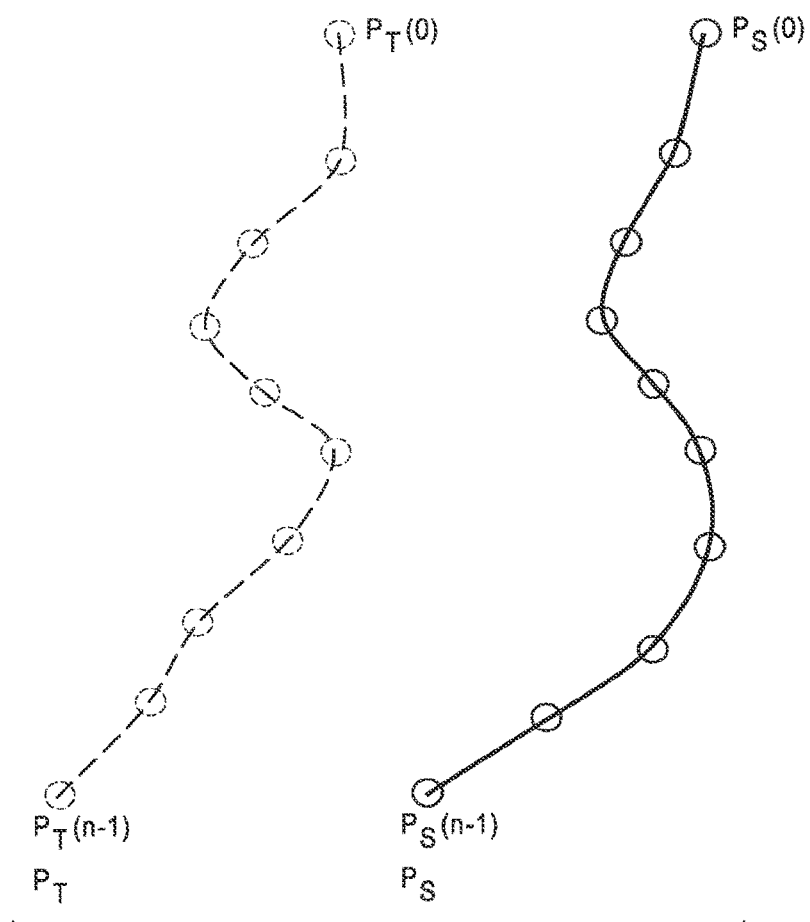

FIG. 14 illustrates point sets used to determine a transformation.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein arc for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
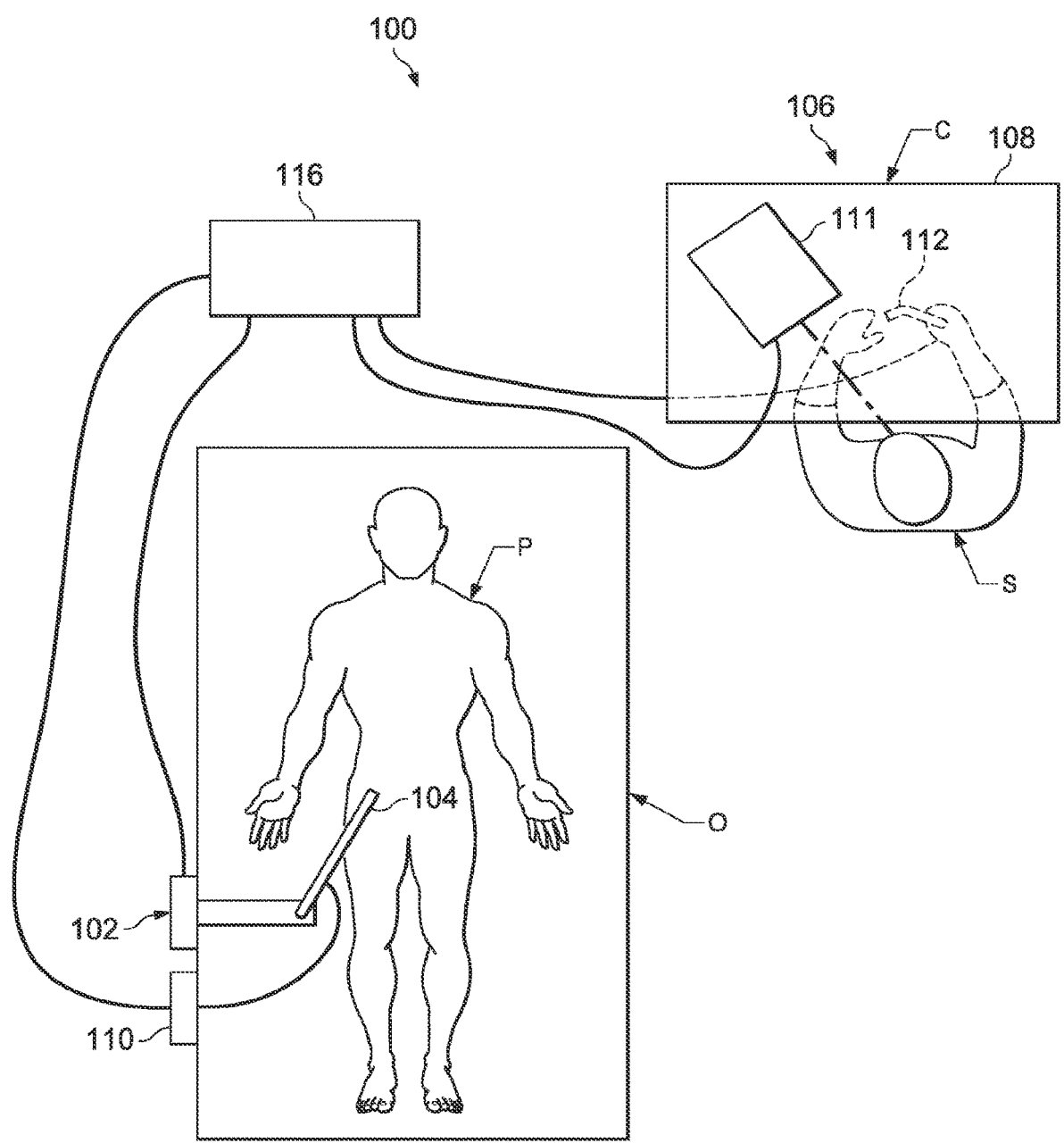
FIG. 1 is a teleoperational medical system, in accordance with embodiments of the present disclosure.

Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments. a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures.

As shown in FIG. 1, the teleoperational system 100 generally includes a teleoperational assembly 102 for operating a medical instrument system 104 in performing various procedures on the patient P. The assembly 102 is mounted to or near an operating table O on which a patient P is positioned. The medical instrument system 104 is operably coupled to the teleoperational assembly 102. An operator input system 106 allows a surgeon or other type of clinician S to view images of or representing the surgical site and to control the operation of the medical instrument system 104.

In alternative embodiments, the teleoperational system may include more than one manipulator assembly. The exact number of manipulator assemblies will depend on the surgical procedure and the space constraints within the operating room among other factors. The operator input system 106 may be located at a surgeon's console C, which is usually located in the same room as operating table O. However, it should be understood that the surgeon S can be located in a different room or a completely different building from the patient P. Operator input system 106 generally includes one or more control device(s) 112 for controlling the medical instrument system 104. The control device(s) 112 may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) 112 will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) 112 may have more or fewer degrees of freedom than the associated medical instruments and still provide the surgeon with telepresence. In some embodiments, the control device(s) 112 are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 116). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system 110 for capturing images from the distal end of the catheter system.

The visualization system 110 may include a viewing scope assembly (described in greater detail below) such that a concurrent or real-time image of the surgical site is provided to surgeon console C. The concurrent image may be, for example, a two or three dimensional image captured by an endoscope positioned within the surgical site. In this embodiment, the visualization system 100 includes endoscopic components that may be integrally or removably coupled to the medical instrument 104. However in alternative embodiments, a separate endoscope, attached to a separate manipulator assembly may be used with the surgical instrument to image the surgical site. The visualization system 110 may be implemented as hardware, firmware, software or a combination thereof which interact with or are otherwise executed by one or more computer processors, which may include the processors of a control system 116 (described below).

The teleoperational medical system 100 also includes a display system 111 for displaying an image or representation of the surgical site and medical instrument system(s) 104 generated by sub-systems of the sensor system 108. The display 111 and the operator input system 106 may be oriented so the operator can control the medical instrument system 104 and the operator input system 106 with the perception of telepresence.

The display system 111 may also display an image of the surgical site and surgical instruments captured by the visualization system 110. The display 111 and the control devices 112 may be oriented such that the relative positions of the imaging device in the scope assembly and the surgical instruments are similar to the relative positions of the surgeon's eyes and hands so the operator can manipulate the surgical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 111 may present images of the surgical site recorded and/or modeled preoperatively using imaging technology such as, computerized tomography (CT), magnetic resonance imaging (MRI), fluoroscopy, thermography, ultrasound, optical coherence tomography (OCT), thermal imaging, impedance imaging, laser imaging, or nanotube X-ray imaging. The presented preoperative images may include two-dimensional, three-dimensional, or four-dimensional images. The presented preoperative or intra-operative images may include two-dimensional, three-dimensional, or four-dimensional (including e.g., time based or velocity based information) images and associated image data sets for reproducing the images.

In some embodiments, the display 111 may display a virtual navigational image in which the actual location of the medical instrument 104 is registered (i.e., dynamically referenced) with preoperative or concurrent images to present the surgeon S with a virtual image of the internal surgical site at the location of the tip of the instrument 104. An image of the tip of the instrument 104 or other graphical or alphanumeric indicators may be superimposed on the virtual image to assist the surgeon controlling the surgical instrument. Alternatively, the instrument 104 may not be visible in the virtual image.

In other embodiments, the display 111 may display a virtual navigational image in which the actual location of the surgical instrument is registered with preoperative or concurrent images to present the surgeon S with a virtual image of surgical instrument within the surgical site from an external viewpoint. An image of a portion of the surgical instrument or other graphical or alphanumeric indicators may be superimposed on the virtual image to assist the surgeon controlling the instrument 104.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intra-operatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
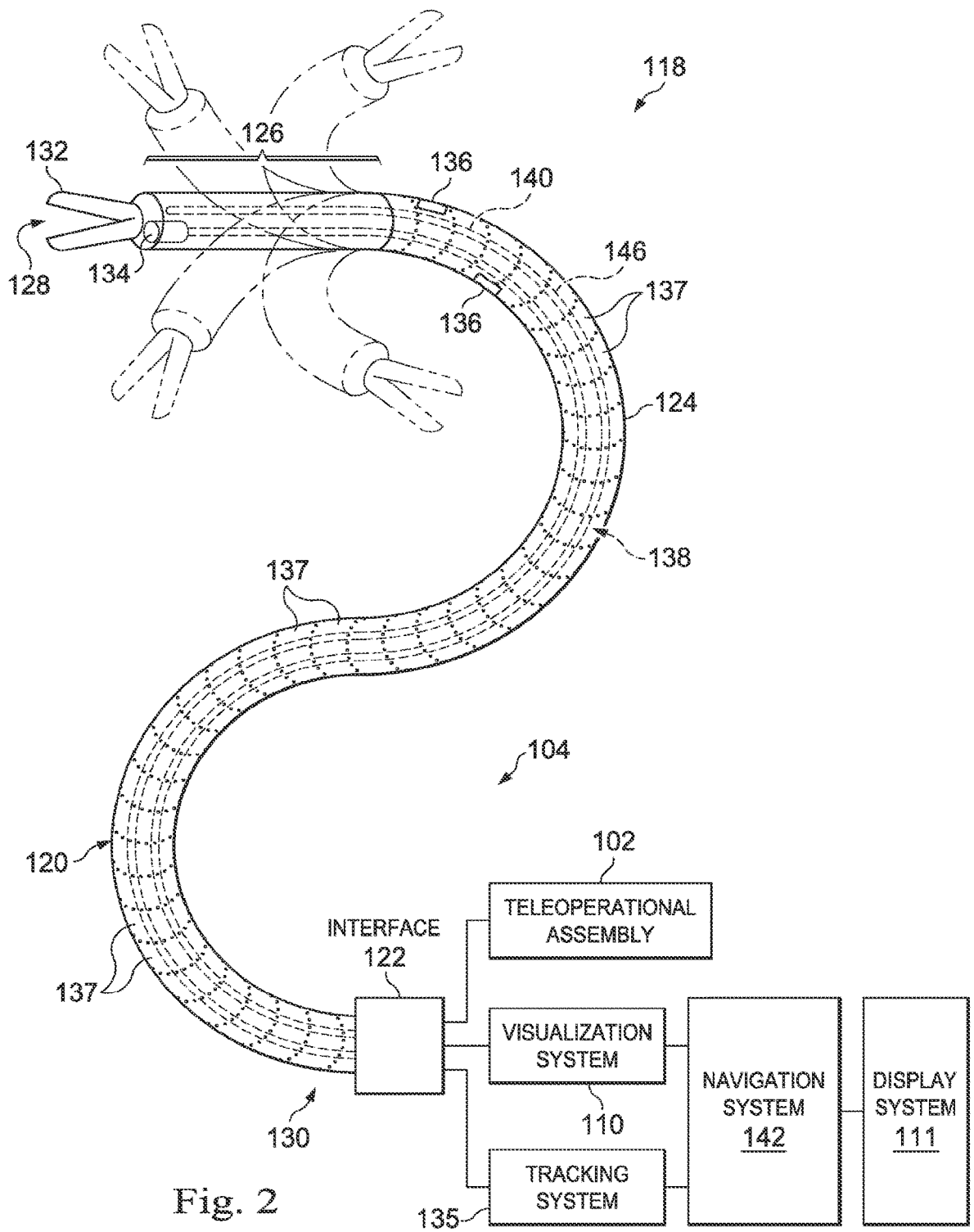
FIG. 2 illustrates a medical instrument system utilizing aspects of the present disclosure.

FIG. 2 illustrates a tracked instrument system 118 which includes the medical instrument system 104 and its interfacing systems. The medical instrument system 104 includes a flexible instrument 120 coupled by an interface 122 to the teleoperational assembly 102 and the visualization system 110. The instrument 120 has a flexible body 124, a tip 126 at its distal end 128, and the interface 122 at its proximal end 130. The body 124 houses cables, linkages, or other steering controls (not shown) that extend between the interface 122 and the tip 126 to controllably bend or turn the tip as shown for example by the dotted line versions of the bent tip 126, and in some embodiments control an optional end effector 132. The flexible instrument may be steerable, including the steering controls previously described, or may be non-steerable with no integrated mechanism for operator control of the instrument bending. The end effector may be a working distal part that is manipulable for a medical function, e.g., for effecting a predetermined treatment of a target tissue. For instance, some end effectors have a single working member such as a scalpel, a blade, an endoscope, or an electrode. Other end effectors such as shown in the embodiment of FIG. 2, have a pair or plurality of working members such as forceps, graspers, scissors, or clip appliers, for example. Examples of electrically activated end effectors include electrosurgical electrodes, transducers, sensors, and the like. End effectors may also include conduits to convey fluids, gases or solids to perform, for example, suction, insufflation, irrigation, treatments requiring fluid delivery, accessory introduction, biopsy extraction and the like). In other embodiments, flexible body 124 can define one or more lumens through which surgical instruments can be deployed and used at a target surgical location. In various embodiments, the instrument 120 may include a flexible bronchial instrument, such as a bronchoscope or bronchial catheter for use in examination, diagnosis, biopsy, or treatment of a lung. The flexible body is also suited for navigation and treatment of other tissues, via natural or surgically created connected passageways, in any of a variety of anatomical systems including the colon, the intestines, the kidneys, the brain, the heart, the circulatory system, or the like.

The instrument 120 can also include an image capture element 134 which may include a stereoscopic or monoscopic camera disposed at the distal end 128 for capturing images that are transmitted to and processed by the visualization system 110 for display by the display system 111. Alternatively, the image capture element 134 may be a coherent fiber-optic bundle that couples to an imaging and processing system on the proximal end of the instrument 120, such as a fiberscope. The image capture element 134 may be single or multi-spectral for capturing image data in the visible or infrared/ultraviolet spectrum.

In the pictured embodiment, the tracking system 135 includes an electromagnetic (EM) sensor system 136 and a shape sensor system 138 for determining the position, orientation, speed, pose, and/or shape of the distal end 128 and of one or more segments 137 along the instrument 120. Although only an exemplary set of segments 137 are depicted in FIG. 2, the entire length of the instrument 120, between the distal end 128 and the proximal end 130 (and including the tip 126) may be effectively divided into segments. The tracking system 135 may be implemented as hardware, firmware, software or a combination thereof which interact with or are otherwise executed by one or more computer processors, which may include the processors of a control system 116.

The EM sensor system 136 includes one or more conductive coils that may be subjected to an externally generated electromagnetic field. Each coil of the EM sensor system 136 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The sensor system 138 includes an optical fiber 140 aligned with the flexible body 124 (e.g., provided within an interior channel (not shown) or mounted externally). The tracking system 135 is coupled to a proximal end of the optical fiber 140. In this embodiment, the fiber 140 has a diameter of approximately 200 tun. In other embodiments, the dimensions may be larger or smaller.

The optical fiber 140 forms a fiber optic bend sensor for determining the shape of the instrument 120. In one alternative, optical fibers including Fiber Bragg Gratings (FBGs) are used to provide strain measurements in structures in one or more dimensions. Various systems and methods for monitoring the shape and relative position of a optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and fluorescence scattering may be suitable.

In other alternative embodiments, the shape of the instrument 120 may be determined using other techniques. For example, if the history of instrument tip's pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the instrument. Alternatively, a series of positional sensors, such as EM sensors, positioned along the instrument can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber 140 may include multiple cores within a single cladding 146. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each H3G comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations arc spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for teleoperational surgery is described in U.S. Pat. No. 7,930,065, filed Jul. 20, 2006, disclosing "Teleoperational Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations, Inc. of Blacksburg, Va.

As described, the optical fiber 140 is used to monitor the shape of at least a portion of the instrument 120. More specifically, light passing through the optical fiber 140 is processed by the tracking system 135 for detecting the shape of the surgical instrument 120 and for utilizing that information to assist in surgical procedures. The tracking system 135 may include a detection system for generating and detecting the light used for determining the shape of the instrument 120. This information, in turn, in can be used to determine other related variables, such as velocity and acceleration of the parts of a surgical instrument. By obtaining accurate measurements of one or more of these variables in real time, the controller can improve the accuracy of the teleoperational surgical system and compensate for errors introduced in driving the component parts. The sensing may be limited only to the degrees of freedom that are actuated by the teleoperational system, or may be applied to both passive (e.g., unactuated bending of the rigid members between joints) and active (e.g., actuated movement of the instrument) degrees of freedom.

The information from the tracking system 135 may be sent to the navigation system 142 where it is combined with information from the visualization system 110 and/or the preoperatively taken images to provide the surgeon or other operator with real-time position information on the display system 111 for use in the control of the instrument 120. The control system 116 may utilize the position information as feedback for positioning the instrument 120. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 2, the instrument 104 is teleoperated within the teleoperational surgical system 100. In an alternative embodiment, the teleoperational assembly 102 may be replaced by direct operator control. In the direct operation alternative, various handles and operator interfaces may be included for hand-held operation of the instrument.

Figure 3A:
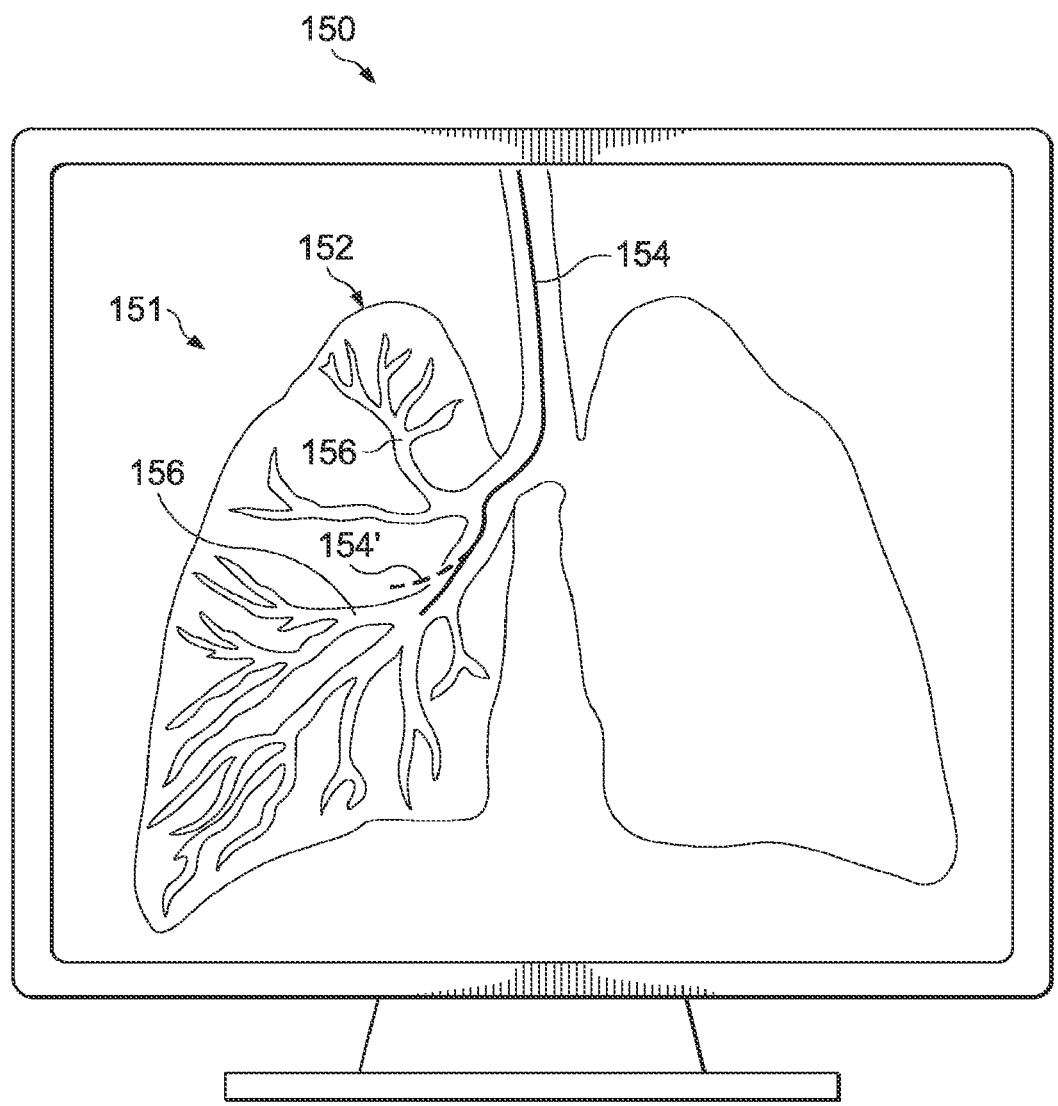
FIG. 3A is an image of a human lung registered with an image of a minimally invasive instrument apparently positioned outside an anatomical passageway.
Figure 3B:
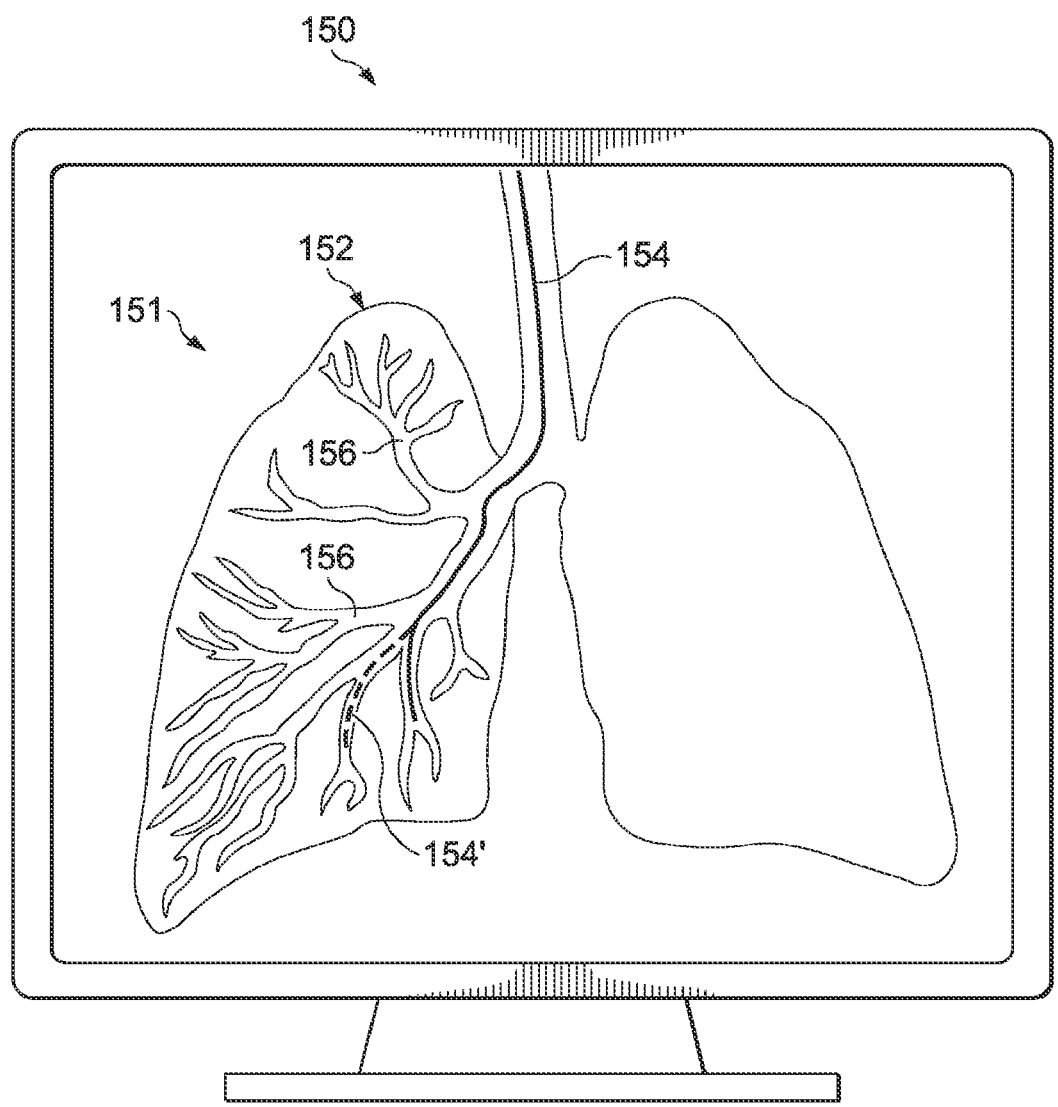
FIG. 3B is an image of a human lung registered with an image of a minimally invasive instrument apparently positioned inside an incorrect anatomical passageway.

FIG. 3A depicts a composite image 150 including an image 151 of a human lung 152, from a viewpoint external to the lung, registered with an instrument image 154 of a flexible instrument, such as the flexible instrument 120. The image 151 of the lung 152 may be generated from preoperatively recorded images or may be generated concurrently during the surgical procedure. The composite image 150 may be displayed via display system 111. As the instrument 120 is advanced through bronchial passageways 156 of the lung 152, information from the tracking system 135 and/or the visualization system 110 is used to register the instrument image 154 with the lung image 151. The image 151 of the lung 152 may change, for example, to depict the lung in a state of inspiration or expiration. The instrument image 154 may change to depict the advancement or withdrawal of the instrument 120 through the bronchial passageways 156. Occasionally, the composite image 150 may erroneously render the instrument image 154 such that a portion of the instrument image 154' is outside of a bronchial passageway (as shown in FIG. 3A) or is positioned within an incorrect bronchial passageway (as shown in FIG. 3B). Systems and methods are described below for correcting the instrument image such that the instrument is located within the correct bronchial passageway.

Figure 3C:
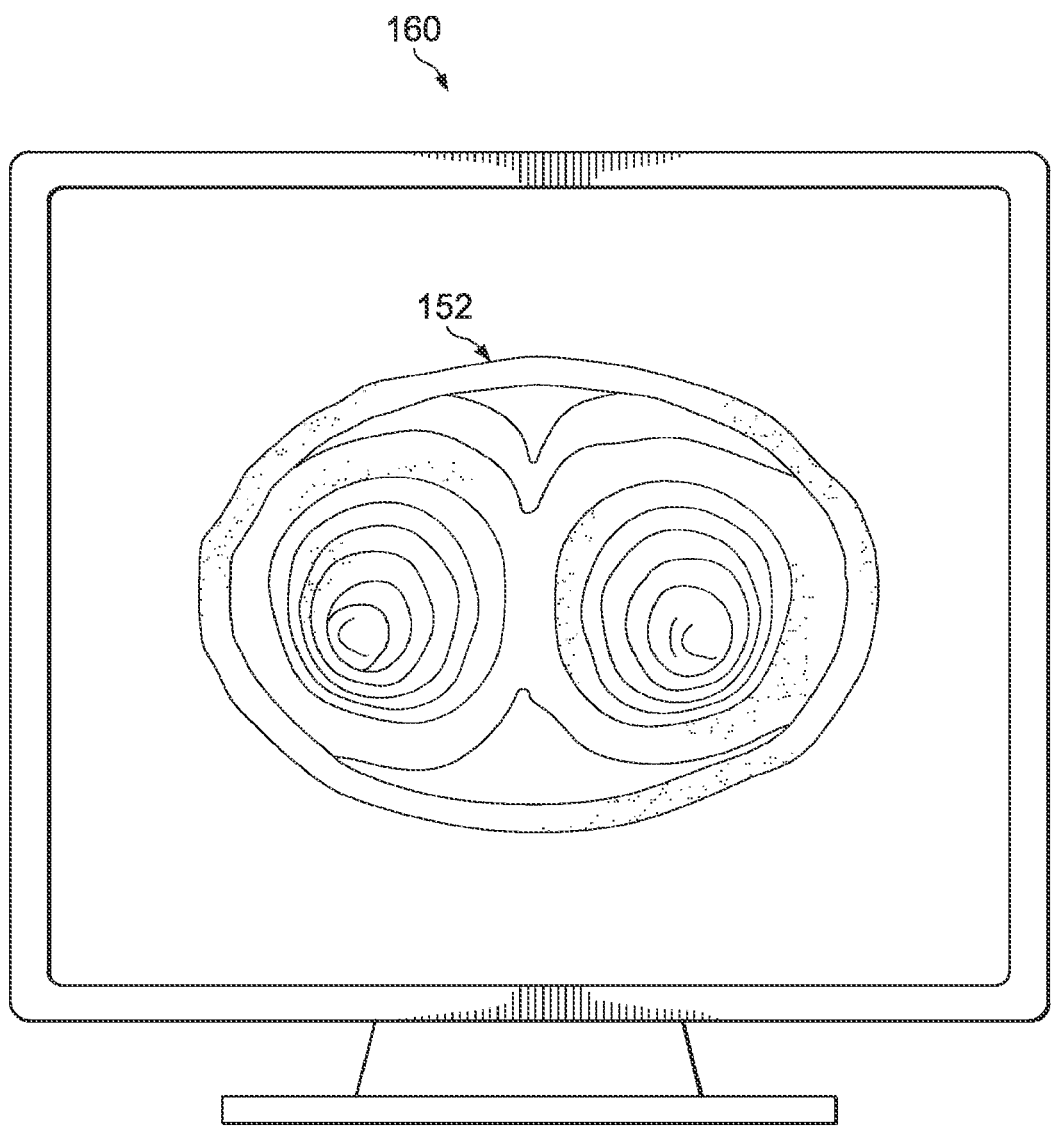
FIG. 3C is an internal image of the human lung depicting the region of the human lung from the viewpoint of the minimally invasive instrument.

FIG. 3C is an internal image 160 of the human lung 152 depicting a region of the lung from the viewpoint of the instrument 120. The image 160 may be a concurrent image taken during the surgical procedure by the instrument 120 while located in the depicted portion of the lung 152. More specifically, the image may be captured by the visualization system 110. Alternatively, the image 160 may be a preoperatively recorded image selected based upon the location of the tip of the instrument 120 as determined by the tracking system 135.

Returning to FIG. 2, the tracking system 135, which includes the EM sensor system 136 and the shape sensor system 138, may calculate a position for the instrument tip 126 or one or more segments 137 of the instrument 120 indicating that the tip is outside the actual anatomical passageway containing the relevant instrument parts (e.g., as being positioned outside the bronchial tree entirely or within the wrong passageway). This likely indicates a slight measurement error (assuming the wall of the anatomical passageway has not been breached). Such an error may result from the dynamic nature of certain anatomic structures such as the lungs or the heart. For example, inhalation and exhalation changes the position and size of the bronchial passageways of the lung. Alternatively, the error may result from patient motion or from tissue deformation caused by the presence of the surgical instrument within the anatomic passageways. In some instances, the error may result from tissue deformation caused by fluid accumulation or tumor growth (e.g., progressive tumor growth since the pre-operative imaging was obtained).

To correct the position of the instrument and accurately locate one or more points of the instrument within the correct passageway when the image of the instrument and the image of the patient anatomy are co-registered and displayed, selected points of the instrument may be snapped or graphically registered to a location on the wall of the anatomical passageway or to the lumen of the anatomical passageway. As will be described in detail below, a variety of compensation methods may be used to correct the model of the patient anatomy to adjust for internal and external deformation forces, patient movement, or other changes in the patient anatomy subsequent to the recording of the preoperative image. Internal deformation forces on tissues of the anatomy may result, for example, from movement between breathing states of inspiration and expiration, cardiac movement, tumor growth, fluid accumulation, and coughing. External deformation threes on tissues of the anatomy may result, for example, from instrument insertion and manipulation. A corrected model of the patient anatomy allows for the generation of a more accurate composite image of the instrument relative to the anatomical passageways.

A corrected model may be particularly useful in the context of virtual navigation inside the anatomical passageways of a patient. Virtual navigation is based upon reference to a preoperatively acquired dataset associated with the three dimensional anatomical structure of the passageways. For example, the dataset may be acquired by a preoperative CT scan. Software is used to convert the CT images into a three dimensional model describing the various locations and shapes of the passageways and their connectivity. During the virtual navigation procedure, the sensor system, particularly the EM sensor system, may be used to compute an approximate location of the instrument with respect to the patient anatomy. Typically an assumption is made that all parts of the patient anatomy are fixed with respect to each other. Under this assumption, a virtual view from the location of the tip of the instrument inside the patient anatomy, as shown in FIG. 3C, can be computed from the preoperative CT scan dataset.

As previously described, the assumption that the patient anatomy remains fixed is generally invalid due to various deformation forces (e.g., both internal and external) applied to the patient anatomy. To compensate for the motion or other errors introduced by the sensor system, a virtual view may be generated from the closest point to the sensed location of the tip of the instrument, inside the passageway, rather than from the computed position of the tip of the instrument. The process of adjusting the location of the sensed location of the instrument to an adjusted location within or on the wall of a passageway is known as snapping. Snapping may work particularly well when passageways are well separated and not densely packed. When deformation forces are large and the passageways are dense (and especially when the passageways have similar curvatures), snapping alone may result in an incorrect choice for the particular airway passage in which the instrument is located.

Figure 4A:
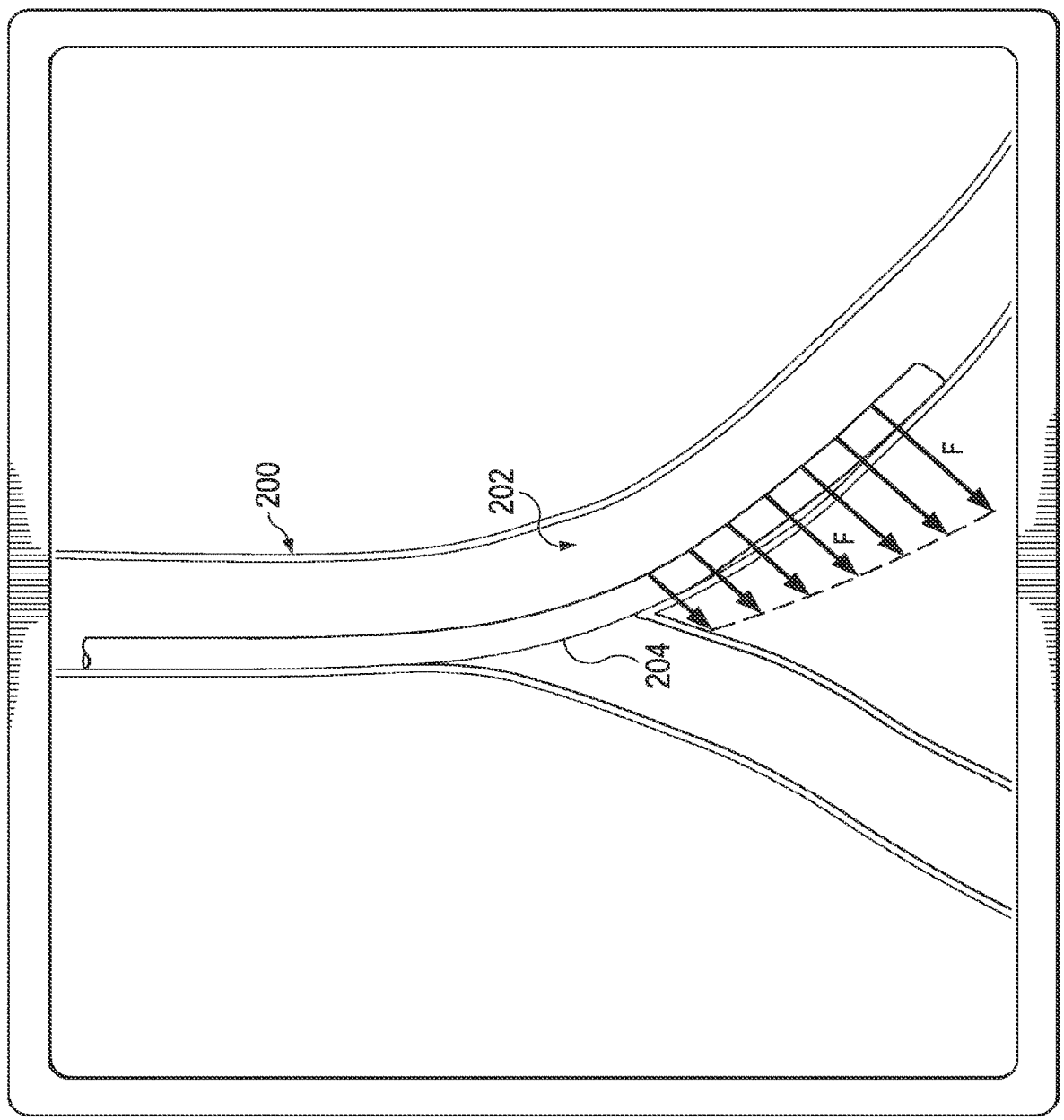
FIG. 4A is an illustration of model of a bronchial passageway of a lung with a catheter.

FIG. 4A is an illustration of an undeformed model 200 of a bronchial passageway 202 of a lung. A catheter 204 extends into the bronchial passageway 202. The catheter 204 may be substantially similar to the instrument 120. The model 2(X) may be displayed on a display system or may reside in an undisplayed form in a computer memory. As shown, the catheter 204 exerts deformation forces F on the bronchial passageway 202.

Figure 4B:
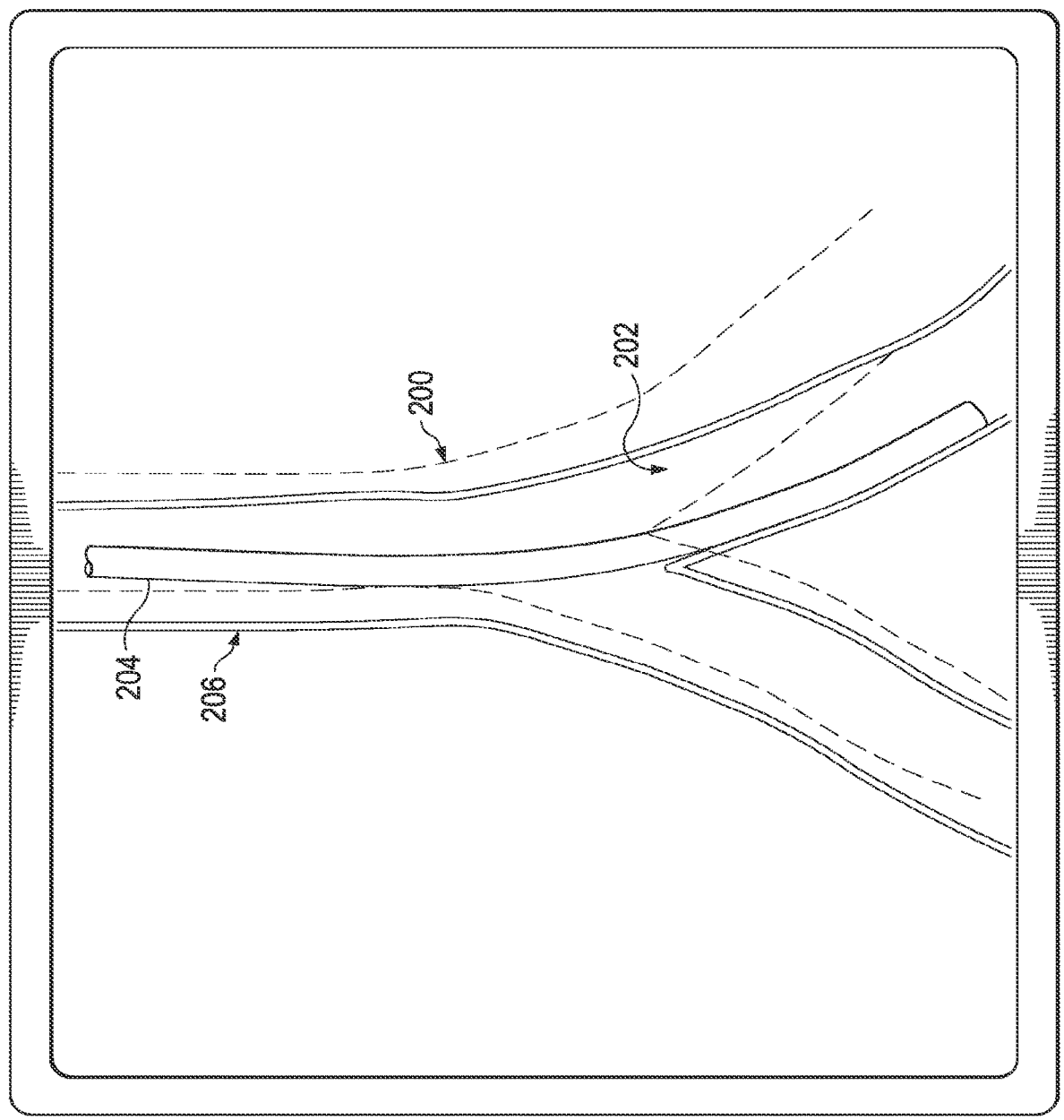
FIG. 4B is an illustration of the model of FIG. 4A adjusted based upon deformation forces applied by the catheter.

FIG. 4B illustrates the effect of the deformation forces F on the model 200. The forces F of the catheter 204 move the bronchial passage 202 from an initial position illustrated by the model 200 to a new position illustrated by a deformed model 206. Thus, the deformed model 206 illustrates the effect of the forces of the catheter 164 on location and orientation of the bronchial passageway 202.

Figure 5A:
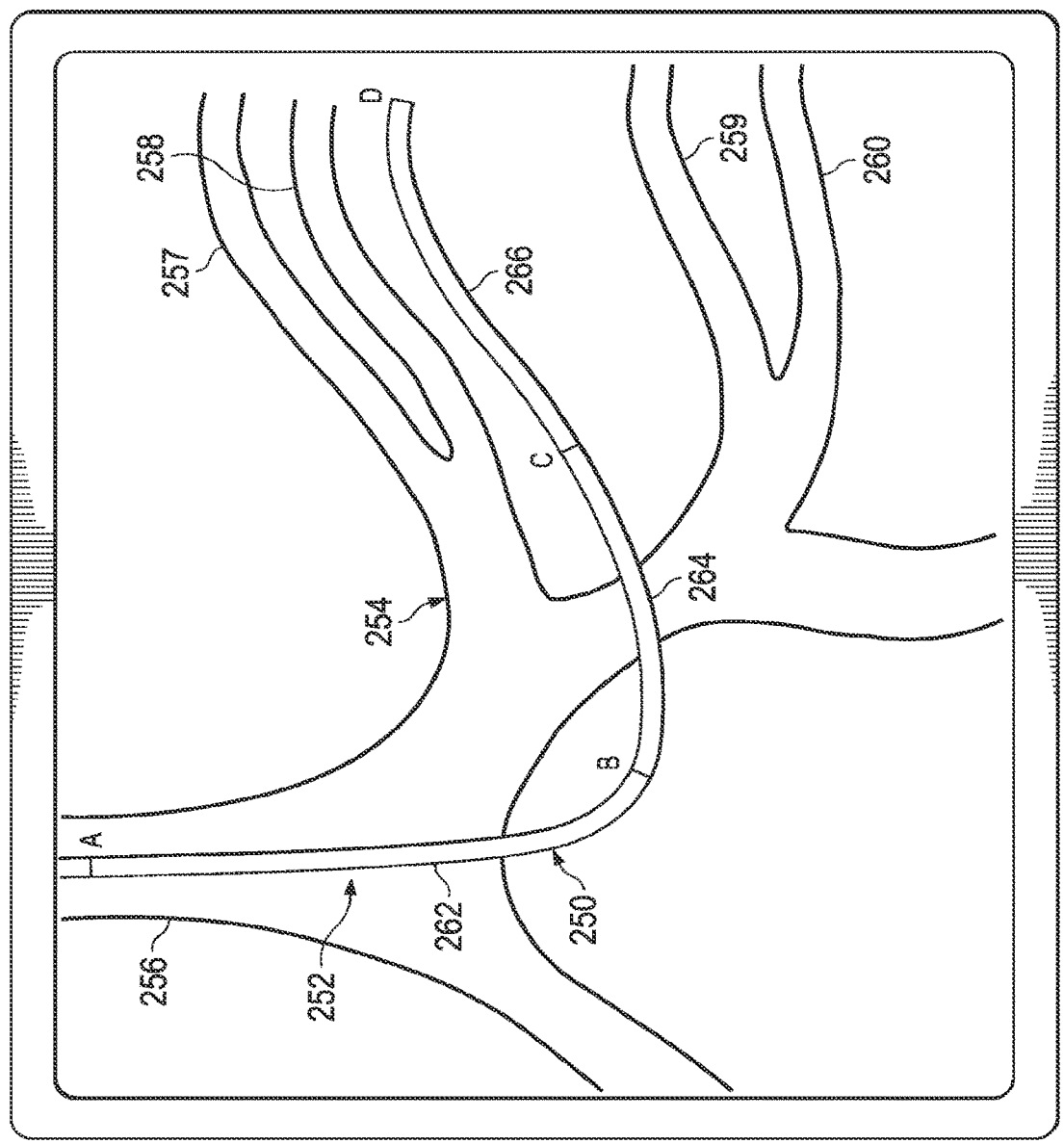
FIG. 5A illustrates a composite image of an undeformed model of bronchial passageways and a sensed model of a catheter.

FIG. 5A illustrates a composite image of a sensed model 250 of a catheter 252 superimposed on an undeformed model 254 of a branched structure of bronchial passageways 256 of a lung. The bronchial passageways 256 of the lung include the distinct passageways 257, 258, 259, and 260. Although the catheter 252 is known to extend into one of the bronchial passageways 257, 258, 259, and 260 (for example through an internal image obtained by the catheter 252 as in FIG. 3C), the sensed model 250 depicts the catheter 252 as positioned outside the passageways 257, 258, 259, and 260. The passageways 257, 258, 259, and 260 may be separated from each other by only a few millimeters, and the passageways 257, 258, 259, and 260 may have very similar curvatures, as shown in FIG. 5A. Merely matching the sensed shape of the catheter 252 to the modeled shape of one of the passageways 257, 258, 259, and 260A may not be sufficient to determine which passageway has actually received the catheter 252. To more accurately determine which passageway has received the catheter 252, a deformed passageway model may be used that takes into consideration the forces exerted on the passageway by varying regions of stiffness of the catheter. This deformed passageway model will depict the effect of the varying forces of the catheter 252 on the location and orientation of the bronchial passageways 256, and thereby correctly depict the position of the catheter 252 relative to the passageways 256.

As will be described in detail below, a process for registering the catheter 252 to an anatomic passageway takes into consideration the deformation forces exerted on the passageway tissue by the active portions of the catheter (i.e., portions under direct operator control) as well as the variably passive portions of the catheter. The process for registration also takes into consideration the anatomical restorative forces associated with the flexibility/rigidity of the passageway tissue and the surrounding tissue. One or more candidate anatomical passageways may be modeled to match the sensed catheter shape and/or tip position. The candidate anatomical passageway(s) may then be evaluated in view of the deformation and restorative forces to determine the most likely matching passageway for registration. This evaluation process includes eliminating any candidate passageways that would not be able to achieve the deformation, as modeled, from the combination of deformation and restorative forces. Alternatively, the candidate anatomical passageways may be modeled to reflect the deformation and restorative forces, and the deformed models may be compared to the catheter shape to identify a matched passageway for registration. Optionally, the model of the matched passageway, as altered by the combination of the deformation and restorative forces, is displayed. Optionally, an image of the catheter may be illustrated in registration with the deformed matching passageway.

Generally, the catheter 252 does not include uniform physical properties along its inserted length. For example, in the pictured embodiment, the catheter 252 includes 3 distinct portions having variable physical properties. In particular, the catheter 252 includes a first section 262 extending from A to B, a second section 264 extending from B to C, and a third section 266 extending from C to D. The catheter 252 has variable stiffness along its length. For example, the first section 262 has a greater stiffness than the second section 264, and the third section 266 comprises an active section having actively controllable stiffness (e.g., upon active steering of the third section 266). In some embodiments, the catheter 252 has a gradually tapered stiffness extending along its length from A to D. Assuming the third section 266 to be the active section, as in the pictured embodiment, the first section 262 may have the tendency to lay on the supporting structure of the passageway 256 while remaining as straight as possible, the second section 264 may have a tendency to comply with the pose of the first section 262 and the surrounding tissue, and the third section 266 may cause local deformation only (e.g., along the length of the third section 266 only). In other words, the deformation forces exerted by the three separate sections 262, 264, and 266 are not necessarily the same or equal. The force exerted on the bronchial passageways 256 by the third section 266 may be significantly stronger than the forces exerted on the bronchial passageways 256 by the sections 262 and 264. At the same time, the force exerted by the third section 266 may be constrained to a smaller area than the forces exerted on the bronchial passageways 256 by the sections 262 and 264. To evaluate candidate matching passageways and to construct an accurate deformed model of the bronchial passageways 256 showing the correct positioning of the catheter 252 within the correct passageway, the effect of the individual sections of the catheter 252 on the separate portions of the bronchial passageways must be determined.

FIGS. 5.B-5D illustrate composite images of the sensed model 250 of the catheter 252 (e.g., based on shape sensor data or cumulative position sensor data) positioned within different passageways of deformed candidate models of the bronchial passageways 256. FIG. 5B illustrates a composite image showing the catheter 252 positioned within the passageway 257' of a deformed model 270 of the bronchial passageways 256. The deformed model 270 assumes that the forces exerted by the separate sections of the catheter 252 caused the passageways 256 to shift downwards such that a lower border 272 of the passageway 257 is shifted downwards by a distance D1 (to appear as the passageway 257' with the lower border 272' in the deformed model 270). If, however, the forces exerted by the separate sections of the catheter 252 and the known tissue restorative forces would not have caused the passageways 256 to shift downwards by a distance D1, the deformed model 270 may be eliminated as a candidate. In other words, in view of the physical properties of the catheter 252 (and in particular the second section 264 and/or the third section 266) and the physical properties of the surrounding tissue, if the catheter 252 would not apply sufficient force to displace the bronchial passageway 257 by the distance D1, the control system 116 (or another part of the system 100) can determine that the hypothetical deformed model 270 is an unlikely candidate for registration with the known shape of the catheter.

Figure 5B:
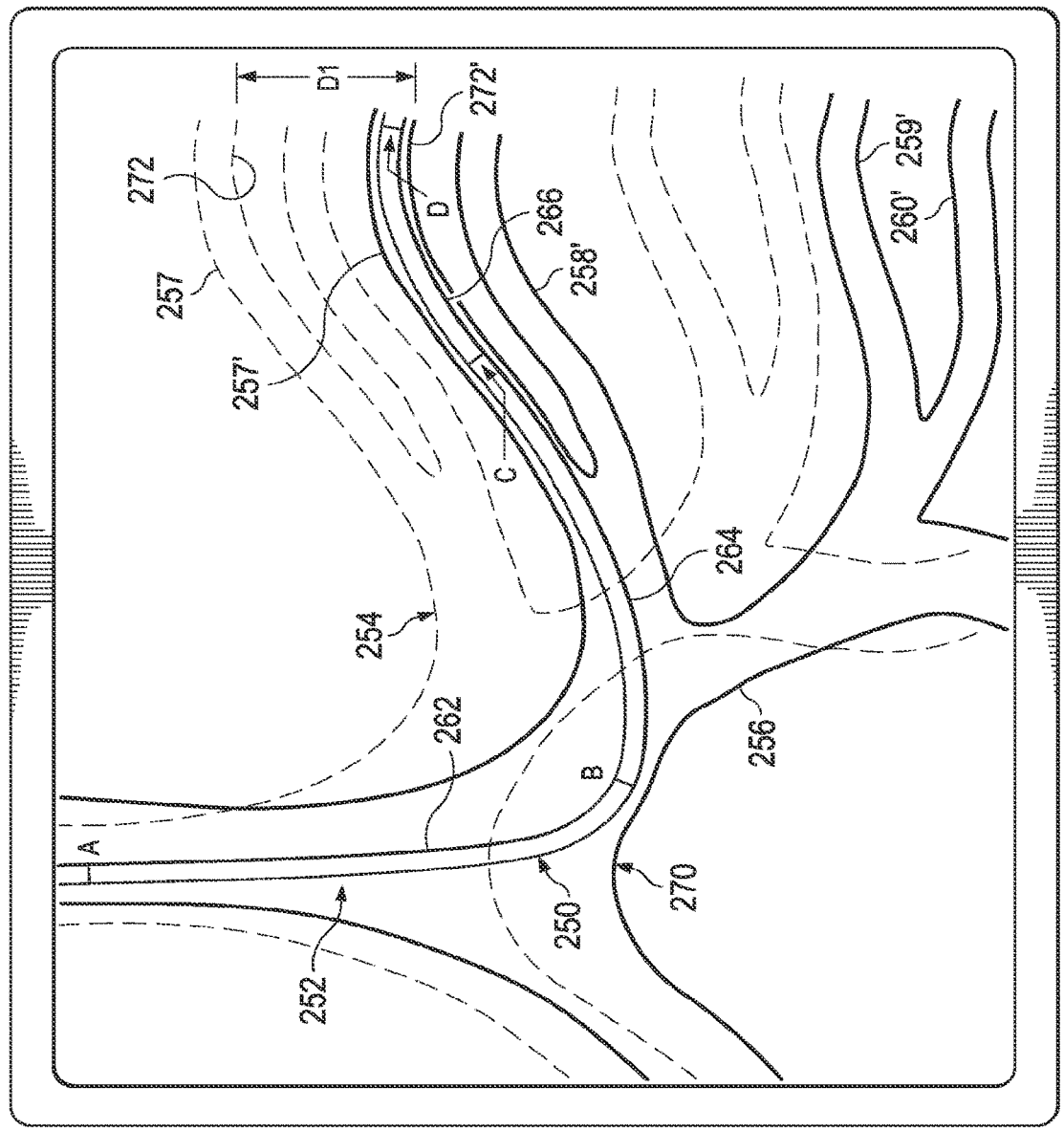
FIGS. 5B-5D illustrate composite images of various deformed models of the bronchial passageways showing the advancement of the catheter into different passageways.
Figure 5C:
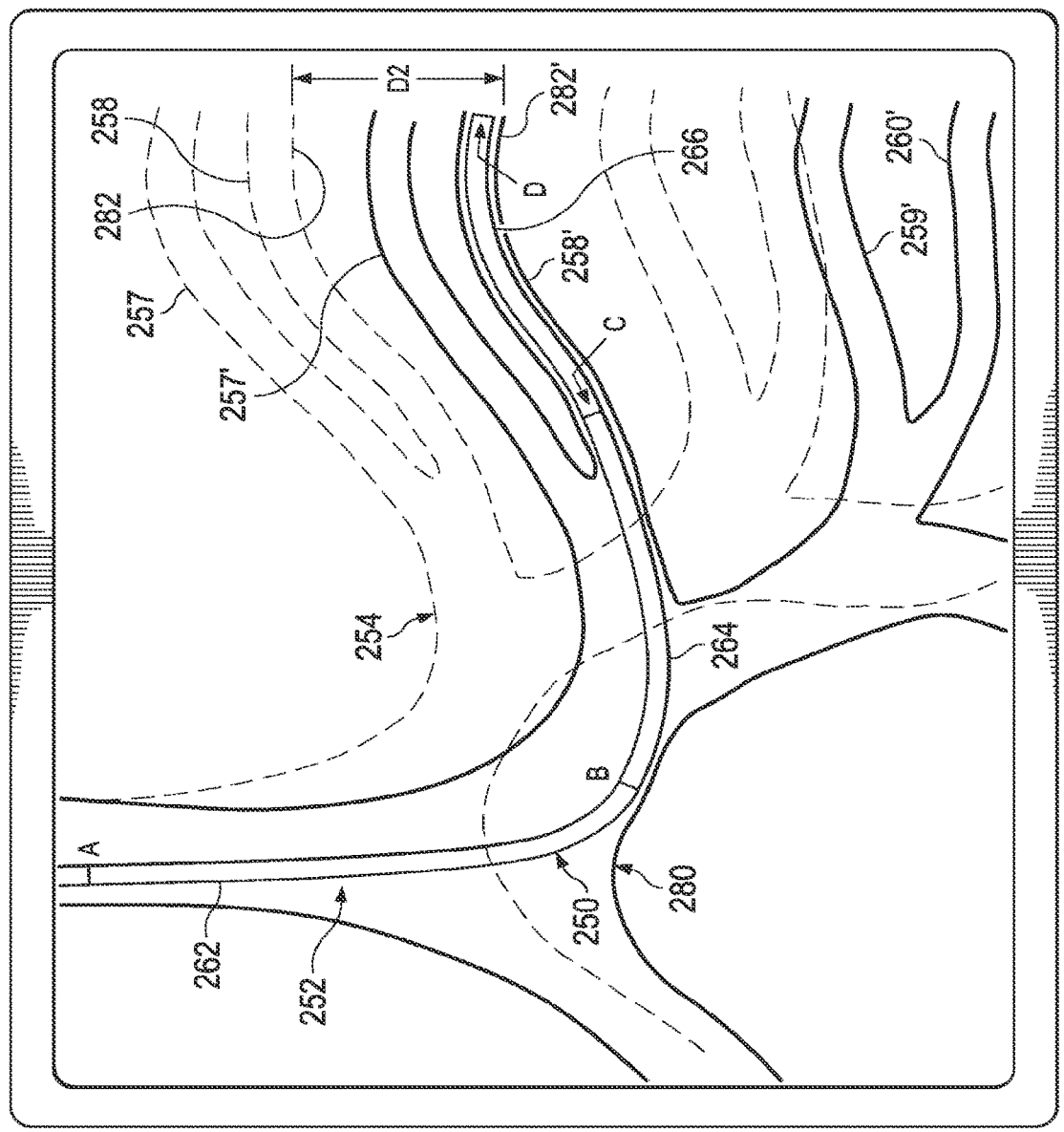

FIG. 5C illustrates a composite image showing the catheter 252 positioned within the passageway 258' of a deformed model 280 of the bronchial passageways 256. The deformed model 280 assumes that the forces exerted by the separate sections of the catheter 252 caused the passageways 256 to shill downwards such that a lower border 282 of the passageway 258 is shifted downwards by a distance D2 (to appear as the passageway 258' with the lower border 282' in the deformed model 280). If, however, the forces exerted by the separate sections of the catheter 252 and the known tissue restorative forces would not have caused the passageways 256 to shift downwards by a distance D2, the deformed model 280 may be eliminated as a candidate. In other words, in view of the physical properties of the catheter 252 (and in particular the second section 264 and/or the third section 266) and the physical properties of the surrounding tissue, if the catheter 252 would not apply sufficient force to displace the bronchial passageway 257 by the distance D2, the control system 116 (or another part of the system 100) can determine that the hypothetical deformed model 280 is an unlikely candidate for registration with the known shape of the catheter.

Figure 5D:
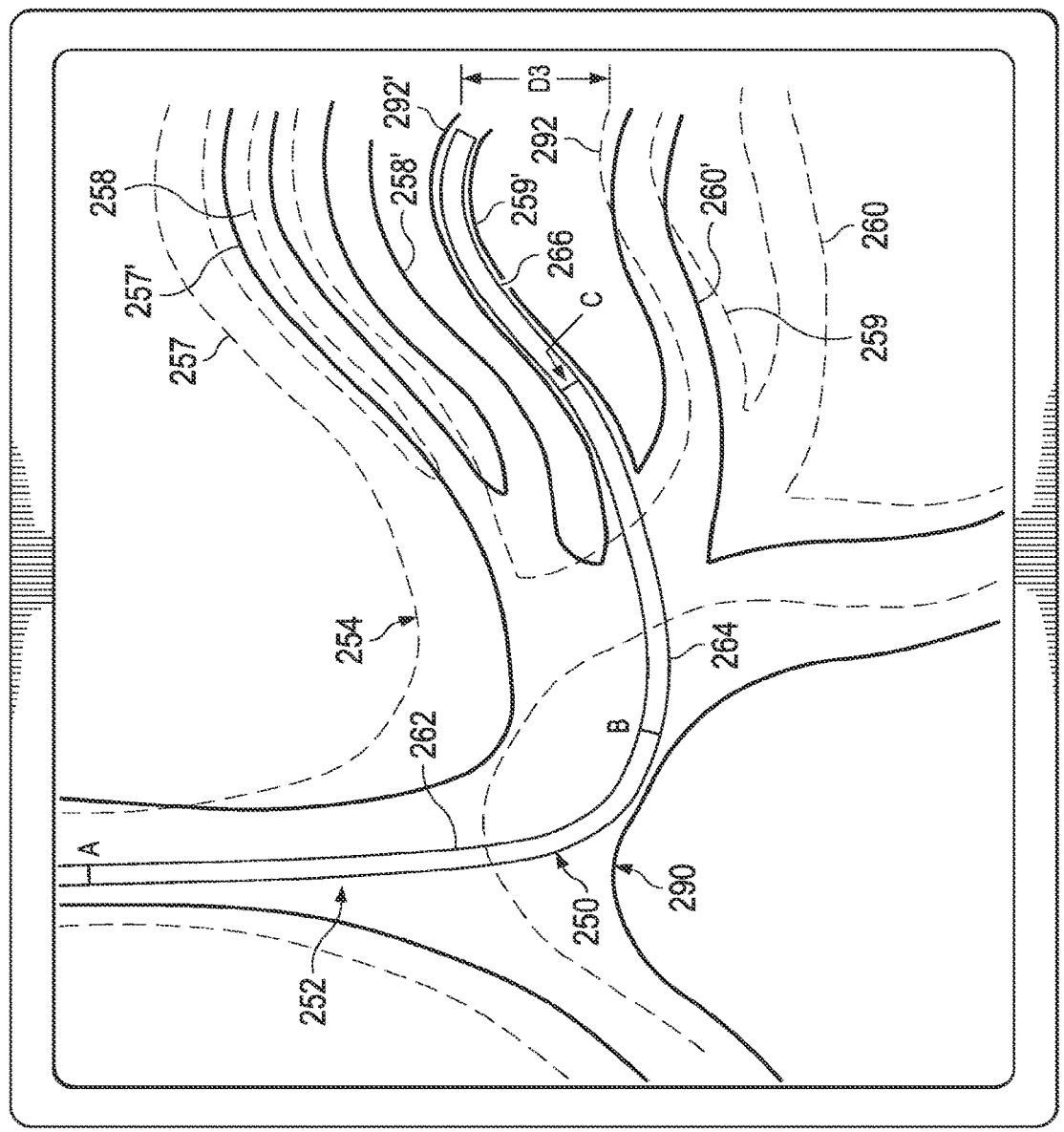

FIG. 5D illustrates a composite image showing the catheter 252 positioned within the passageway 259' of a deformed model 290 of the bronchial passageways 256. The deformed model 290, assumes that the forces exerted by the separate sections of the catheter 252 caused the passageways 259, 260 to shift upwards such that an upper border 292 of the passageway 259 is shifted upwards by a distance D3 (to appear as the passageway 259' with the upper border 292' in the deformed model 290). If, however, the forces exerted by the separate sections of the catheter 252 and the known tissue restorative forces would not have caused the passageway 259 to shift upward by a distance D3, the deformed model 290 may be eliminated as a candidate. In other words, in view of the physical properties of the catheter 252 (and in particular the second section 264 and/or the third section 266) and the physical properties of the surrounding tissue, if the catheter 252 would not apply sufficient force to displace the bronchial passageway 259 upward by the distance D3, the control system 116 (or another part of the system 100) can determine that the hypothetical deformed model 290 is an unlikely candidate for registration with the known shape of the catheter.

After the unlikely candidate models are eliminated, the remaining candidate models may be evaluated to determine which one is the most likely model to match the sensed catheter, based upon the deformation and restorative forces. Although FIGS. 5B-5D illustrate the candidate matching process, it is understood that the process may be conducted by the control system 116 without display of each of the candidate deformation models. When a deformed model is finally selected for registration with the catheter, the deformed model and registered catheter may be displayed.

In various alternative embodiments, the candidate matching process may be illustrated for display.

Figure 6:
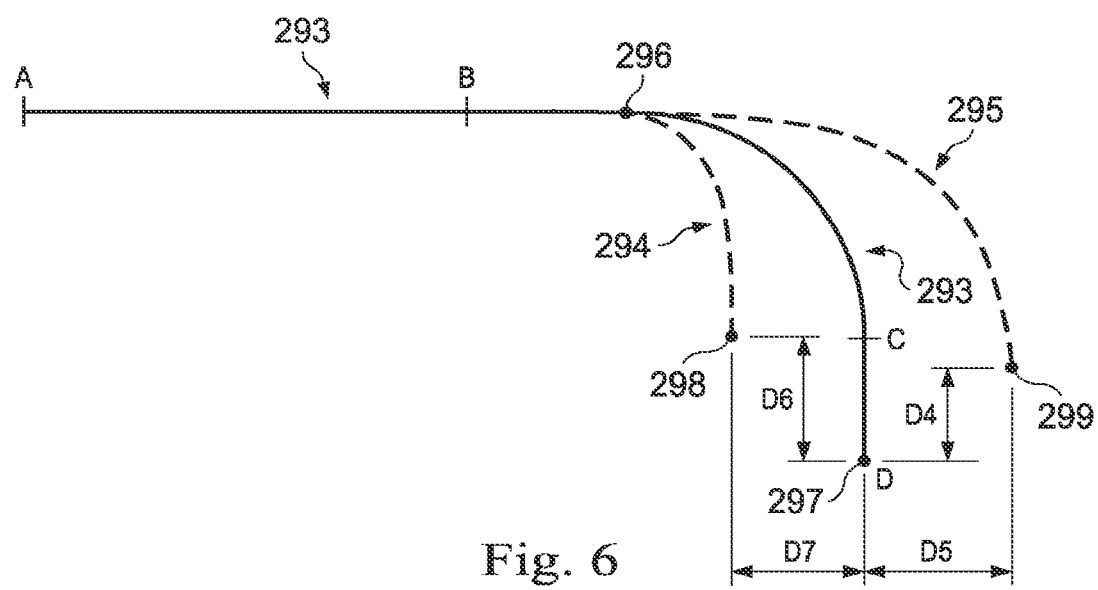
FIG. 6 is a diagram of a sensed model of the catheter shown in FIGS. 5A-5D in comparison with two different models representing two possible passageways that could contain the catheter.

FIG. 6 illustrates a diagrammatic representation of a sensed shape or model 293 of the catheter 252 shown in FIGS. 5A-5D in comparison with two different candidate models 294 and 295 representing two possible passageways that may contain the catheter 252. As shown, merely comparing the sensed shape of the catheter 252 may not be adequate to determine the correct passageway because the two models 294 and 295 have substantially similar curvatures. In particular, the curvature of the sensed shape 293 of the catheter 252 extending between points 296 and 297 is substantially similar to the curvature of the model 294 extending between points 296 and 298, as well as the curvature of the model 295 extending between points 296 and 299. Thus, to determine the correct position of the catheter 252, the control system 116 can compare (e.g., using one or more algorithms of the control system 116) the sensed shape 293 of the catheter 252 with the candidate models 294 and 295, and also factor in the physical characteristics of the different sections of the catheter 252 (e.g., the sections 262, 264. and 266) and the physical characteristics of the tissue surrounding the different sections of the catheter 252. The physical characteristics of the catheter 252 associated with deformation forces include, by way of non-limiting example, the degree of stiffness of the different sections, the force applied by each section (and in particular the active section at the tip or section 266), the direction of the forces applied by each section, and the material composition and weight of the catheter sections. The physical characteristics of the tissue associated with restoration forces include, by way of non-limiting example, the tissue type, the composition of the tissue (e.g., including the fluid or air content of the tissue), the compliance of the tissue, and the adjacent supporting tissue (e.g., bone, muscle, and/or vessels).

By employing such a comprehensive comparison, the control system 116 can determine the correct passageway in which the catheter 252 (e.g., the distal section 266 of the catheter 252) resides. For example, if, based upon the known deformation and restorative forces, the catheter 252 would not be able to shift the point 299 of the model 295 downward by a distance D4 to the point 297 or that the catheter 252 would not be able to shift the model 295 laterally by a distance D5 to the point 297, then the control system 116 may conclude that the candidate model 295 is an unlikely passageway to contain the catheter (as well as any other passageways located above or more lateral to the passageway represented by the model 295). Similarly, if the catheter 252 would not be able to shift the point 298 of the model 294 downward by a distance D6 to the point 297 or that the catheter 252 would not be able to shift the model 295 laterally by a distance D7 to the point 297, then the control system 116 may conclude that the model 294 is an unlikely passageway to contain the catheter (as well as any other passageways located above or more lateral to the passageway represented by the model 294). After eliminating candidate models, a remaining candidate model that conforms to the known deformation and restoration forces may be selected for registration with an image of the catheter. Because the sensed model 293 of the catheter 252 may be inaccurate to a certain degree, the control system 116 may evaluate these sensor values within a pre-defined range of possibilities to account for such inaccuracies.

Figure 7A:
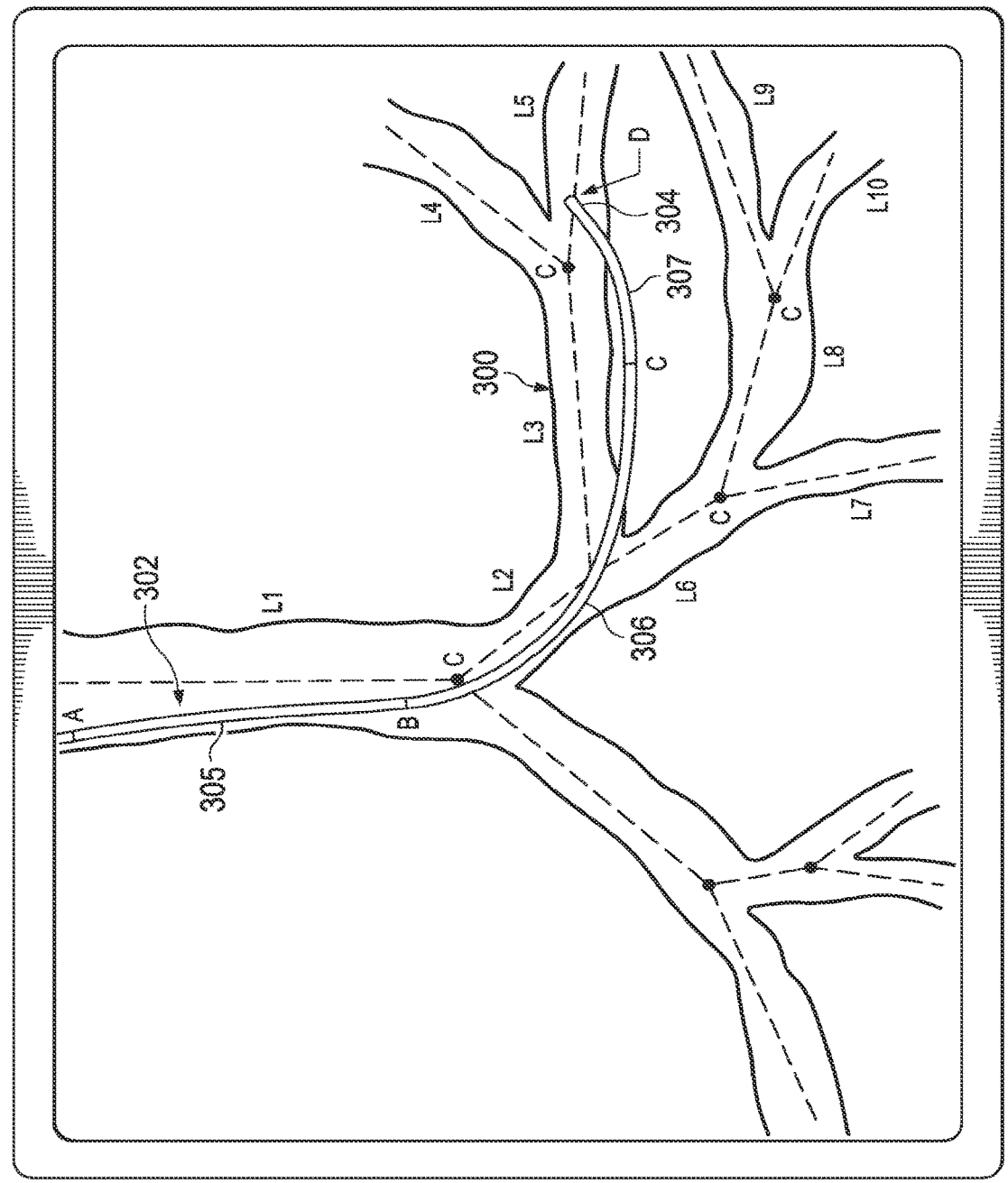
FIG. 7A illustrates a composite image of an undeformed model of bronchial passageways and a sensed model of a catheter.

FIG. 7A illustrates a composite image of an undeformed model 300 of a branched structure of bronchial passageways and a catheter 302 extending through the passageways. With the undeformed model 300, the catheter 302 is shown extending outside of the passageways and a tip 304 of the catheter 302 appears, in the composite image, to be located within the bronchial passageway L5. The catheter 302 may be the same as the catheter 252 shown in FIGS. 5A-5D. For example, in the pictured embodiment, the catheter 302 includes a first section 305 extending between the points A and B, a second section 306 extending between the points B and C, and a third section 307 extending between the points C and D.

As shown in FIG. 7A, the bronchial passageways are modeled as a set of rigid links L1-L10 connected by joints that can rotate around deformation points such as connection points C in both pitch and yaw directions. In some embodiments, other degrees of freedom such as stretch and roll may be accommodated. In other embodiments, joints or other types of deformation points may be located along the lengths of the links L1-L10) to allow multiple locations for bending along the length of the links. In some embodiments, the deformation points may be distributed throughout the modeled links L1-L10, without regard to the location of connection points. The tissue types and the tissue composition of the links and their immediately surrounding tissue can vary significantly. Thus, the individual links may have different physical properties that respond differently to the forces applied by the catheter 302. The curvature of the links L3-L4 and the curvature of the links L8-L9 are substantially similar. From the undeformed model 300, it is unclear whether the sections 306 and 307 of the catheter 302 extend into the links L3-L4 or the links L8-L9. In order to determine whether the sections 306 and 307 of the catheter 302 extend into the links L3-L4 or the links L8-L9, the control system 116 can use the process discussed above in relation to FIGS. 5A-6 to evaluate the possible deformation models in light of the physical properties of the different catheter sections in addition to the physical properties of the tissue with which the catheter interacts.

To deform the model 300 and correct for the forces applied by the catheter, the shape of the whole catheter in the bronchial passageways is determined. A shape sensor system, such as the shape sensor system 138 may be used to determine the shape of the entire catheter, not just the tip. The shape of the catheter is used to determine a set of deformation variables (e.g., pitch and yaw angles) at each connection point C in the undeformed model. The methods used to convert the modeled pitch and yaw angles of the connection points to the poses of the links in the bronchial structure are standard kinematic methods found, for example in Siciliano et al., *Springer Handbook of Teleoperationals* (Springer, 2008). The amount of deformation of the bronchial passageways is determined by virtual forces caused by points of the catheter depicted outside the passageways in the undeformed model as well as the opposing forces caused by the anatomy itself (e.g., the links of the bronchial passageways and their surrounding tissue). The catheter forces act differently along the length of the catheter (e.g., different forces are exerted by the section s 305, 306, and 307) and effectively act to shift the passageway in the direction of the catheter. The amount of deformation is also determined by the opposing or counteracting restorative forces, such as the rigidity of the bronchial passageway and the surrounding connective tissue, which bias the passageway toward the undeformed shape and configuration.

Figure 7B:
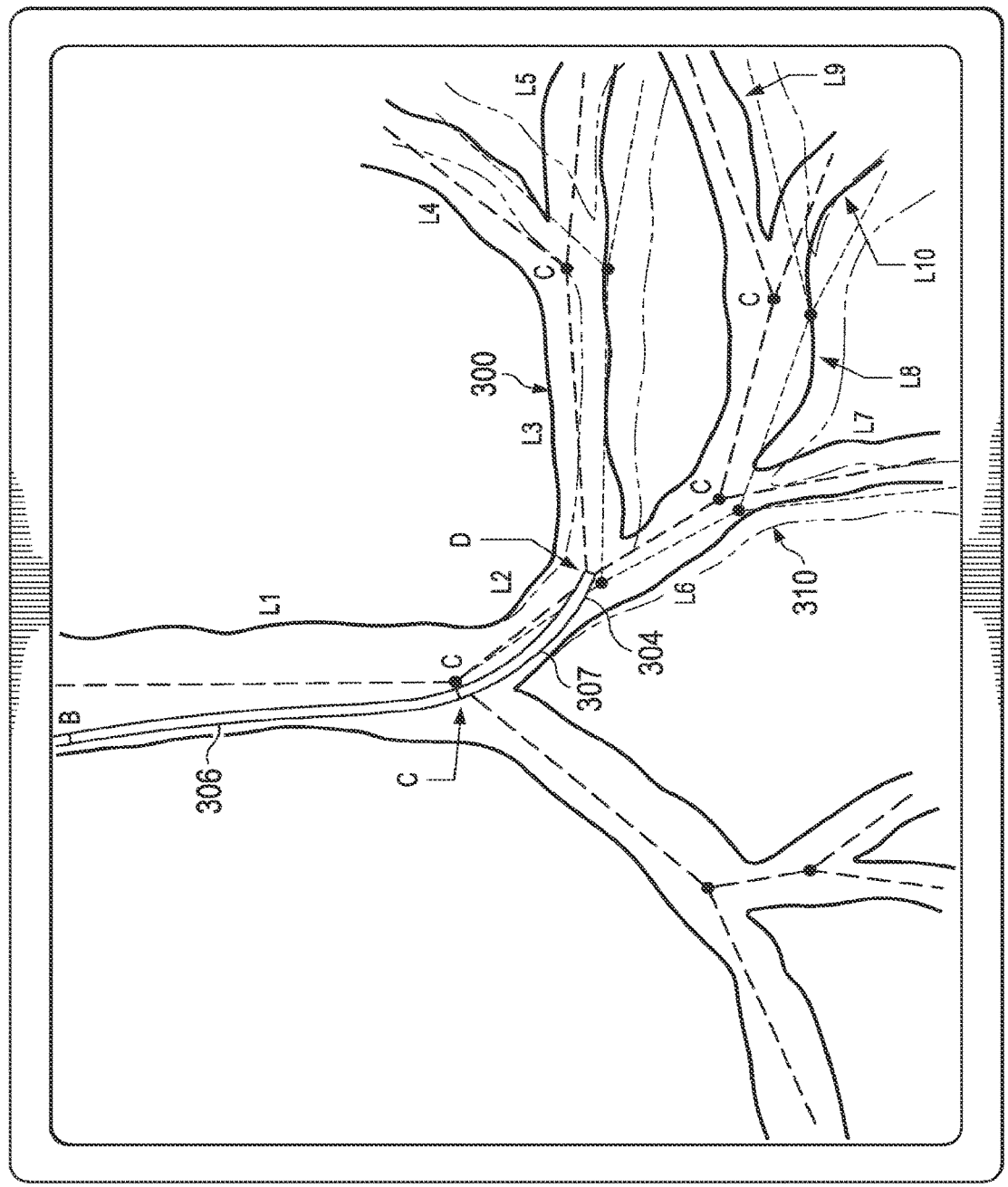
FIGS. 7B-7D illustrate composite images of the model of the bronchial passageways adjusted with the advancement of the catheter.
Figure 7C:
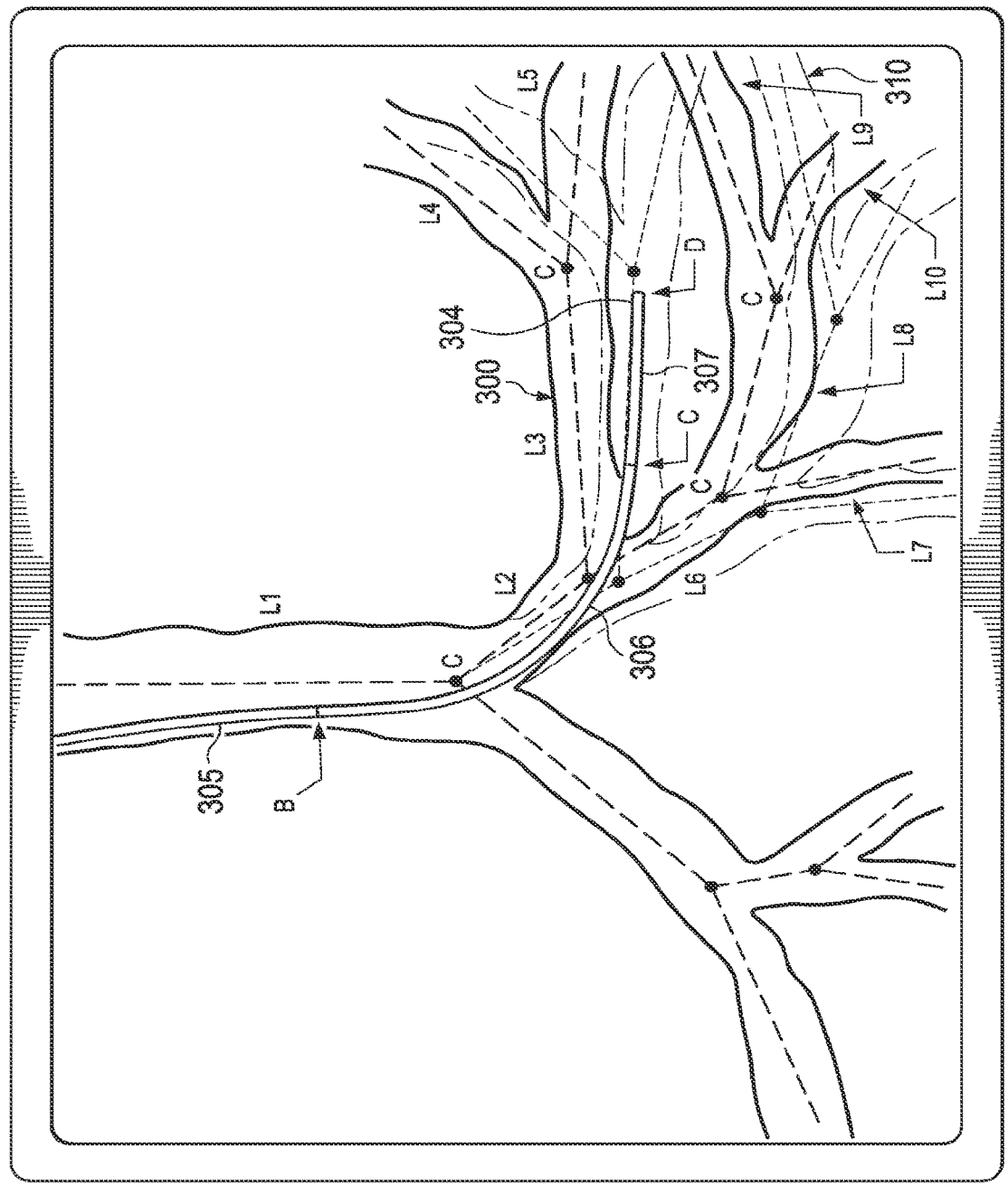
Figure 7D:
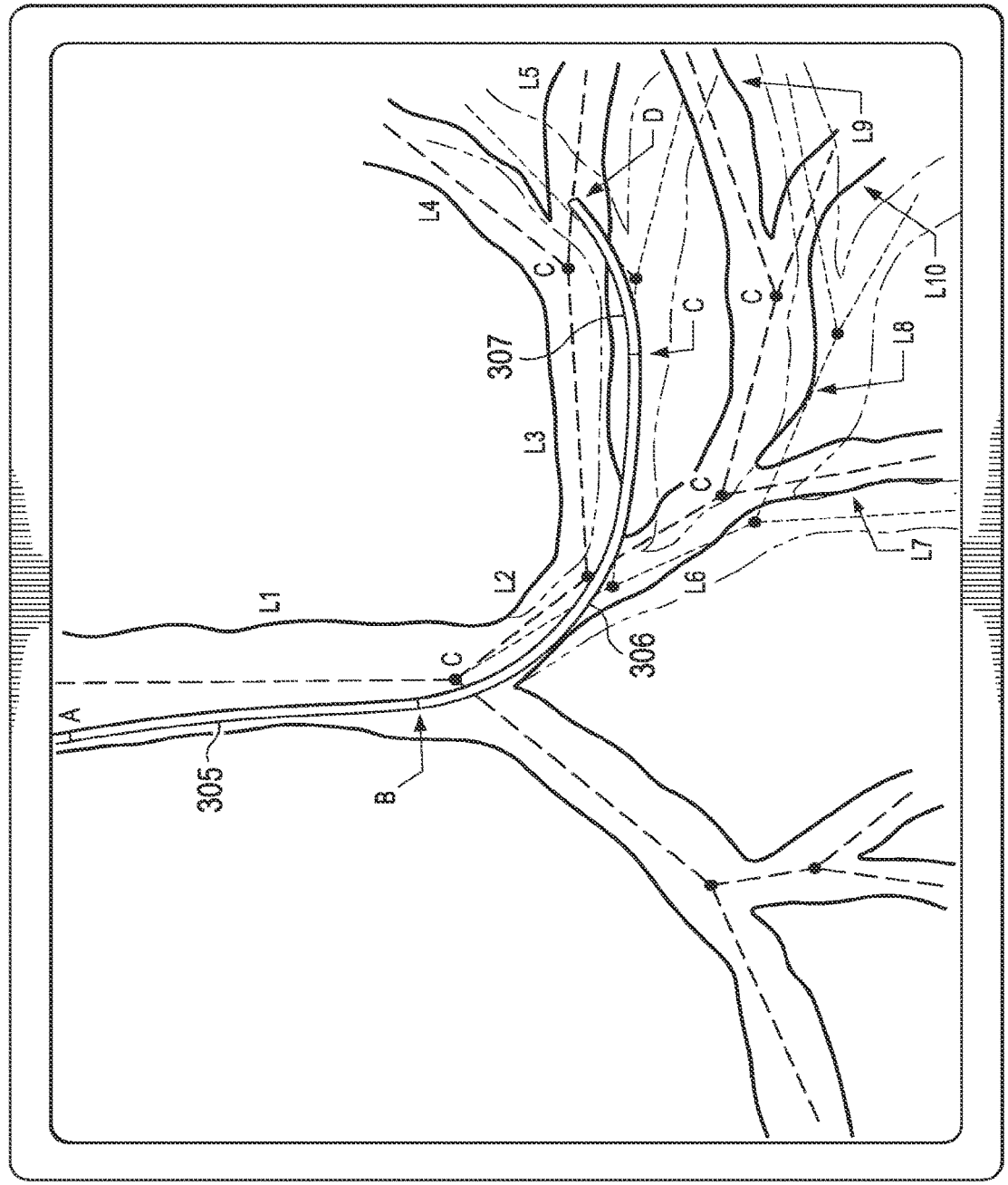

FIGS. 7B-7D depict the undeformed model 300 of the branched bronchial passageways and also show a candidate deformation model 310 of the branched bronchial passageways as the catheter 302 is advanced through the passageways. In FIG. 7B, the catheter 302 is advanced through link L1 and into link L2. The deformation model 310 is shifted slightly from the undeformed model 300 to adjust for the direct forces of the section 307 of the catheter 302 on the links L1, L2 and indirect forces on the connected distal links L3-L10, as well to adjust for the opposing forces of the tissue at links L1 and L2 (and, to a lesser extent, the more distal links). The tip 304 is depicted as within the link L2 in both the undeformed model 300 and the deformed model 310, but the exact location of the tip 304 within the link L2 is different between the two models.

In FIG. 7C, the catheter 302 is advanced through link L2 and into link L3. The candidate deformation model 310 is further shifted from the undeformed model 300 to adjust for the direct forces of the section 306 of the catheter 302 on the links L1, L2, L3, the direct forces of the section 307 of the catheter 302 on the link L3, and indirect forces on the connected distal links L4-L10, as well to adjust for the opposing forces of the tissue at links L1-L3 (and, to a lesser extent, the more distal links). The tip 304 is depicted as outside the link 13 in the undeformed model 3(X) but within the link L3 in the deformed model 310. Thus, the deformed model 310 more accurately reflects the reality that the tip 304 is inside the bronchial passageway.

If, however, the link L3 would not be displaced to where the tip 304 is sensed (within a range of sensor inaccuracy), then the control system 116 may conclude that the candidate deformed model 310 may be eliminated. For example, based on the physical properties of the sections 306 and 307 of the catheter 302, the forces exerted by those sections, and the tissue characteristics and opposing forces of the links L6-L8, the possibility of the tip 304 of the catheter 302 extending into the links L6 and L8 may be evaluated instead. In performing such an evaluation, the control system 116 may construct another candidate deformation model for the catheter 302 extending into the links L6 and L8. In some embodiments, the control system 116 constructs both possible models (e.g., one showing the catheter 302 lying within links L3 and L4 and another showing the catheter 302 lying within the links L6 and L8) immediately after the recognizing that both models are candidates based upon the shape of the catheter 302. In other embodiments, the control system 116 initially constructs the deformed model that appears most likely (e.g., based on curvature comparisons and/or lines of best-fit between the catheter and the passageways), evaluates this model for accuracy, and only constructs the second model if this model is determined to have a certain degree of error or uncertainty below a predefined threshold (e.g., less than a 5% chance of error).

Figure 8:
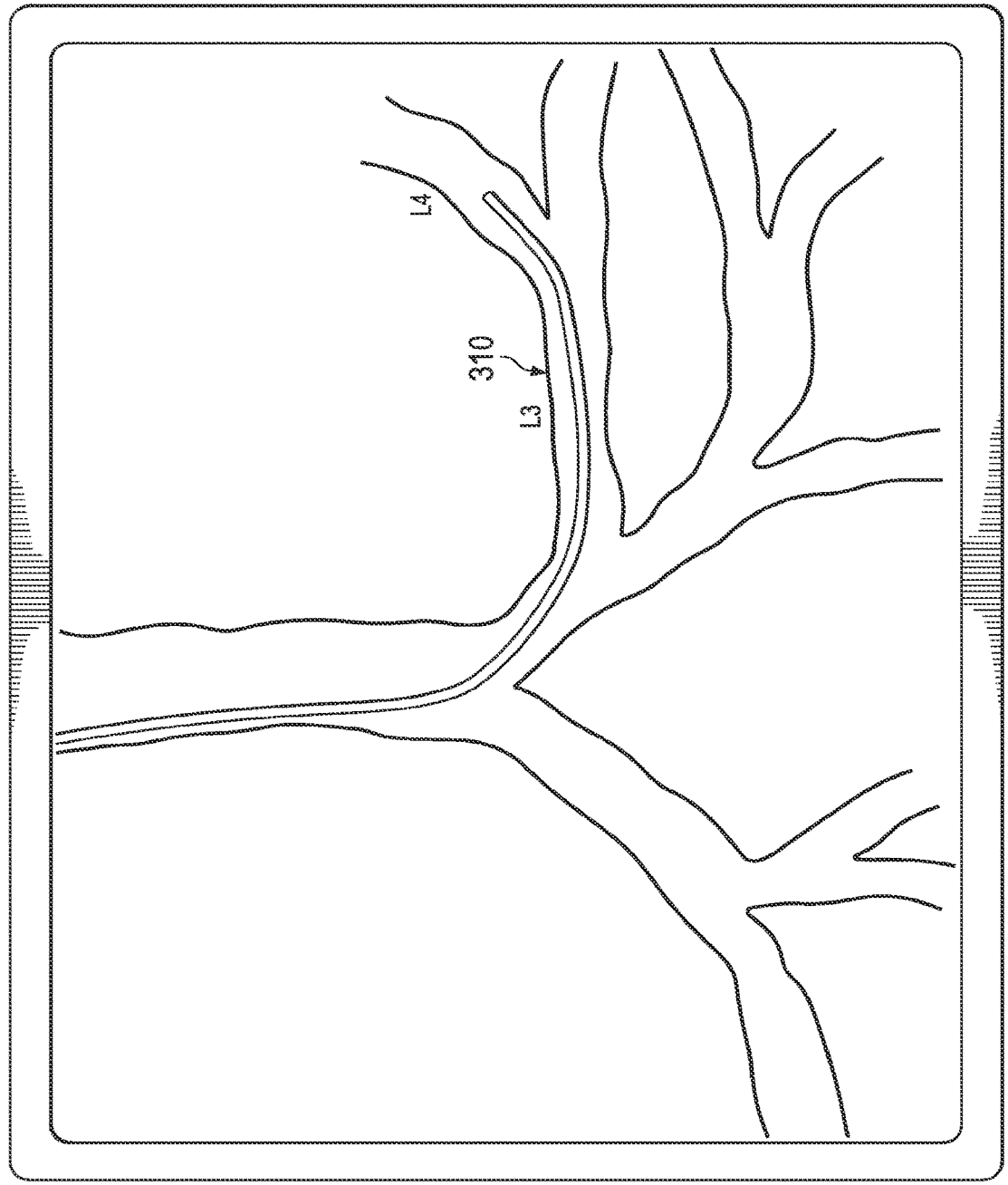
FIG. 8 illustrates a composite image of a deformed model of the bronchial passageway and the catheter shown in FIGS. 7A-7D.

In FIG. 7D, the catheter 302 is advanced into link L4. The deformation model 310 is further shifted from the undeformed model 3(X) to adjust for the direct forces of the catheter 302 on the links L1, L2, L3, L4 and indirect forces on the connected distal links L5-L10. The tip 304 is located in link L5 in the undeformed model 300 and inside the link L4 in the deformed model 310. The control system 116 can confirm that the deformed model 310 is an accurate depiction of the positioning of the catheter 302. Based on the forces applied by each individual section of the catheter 302 on the different links of the bronchial passageways, and the opposing forces applied by each link of the bronchial passageways, the degree of accuracy of the deformed model may be determined. If the deformed model is determined to be accurate and a calculated chance of inaccuracy is below a predefined threshold of error, the control system 116 can conclude that the deformed model 310 more accurately reflects the actual location of the tip 304. The final deformed model 310 may be displayed as depicted in FIG. 8. It is understood that the candidate model evaluation process may be performed by the control system 116 without display until the matched model is determined.

Figure 9:
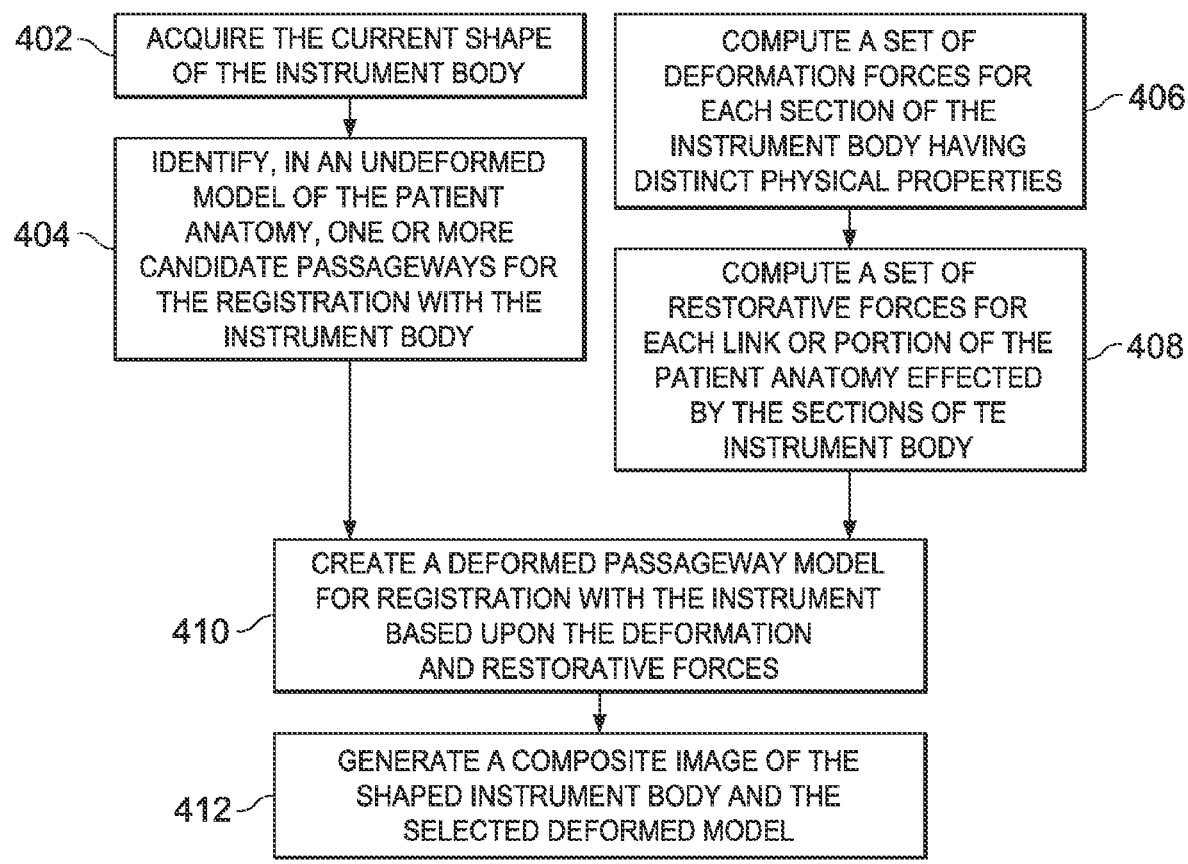
FIG. 9 is a flowchart illustrating a method for deforming a model of anatomic passageways based upon the shape of the catheter, the deformative forces applied by the different sections of the catheter, and the restorative forces of the passageways.

One embodiment of a method for correcting an undeformed model into a more accurate deformed model is provided in the flowchart 400 of FIG. 9. The model may be generated from stored data describing the patient anatomy, for example, from preoperative images, from two or three dimensional datasets describing the patient anatomy, from a standard (i.e., not patient specific model), or from hybrids of any of the above. Initially the deformed model is equal to the static, undeformed model with all deformation variables (e.g., pitch/yaw angles, stretch) set at zero. At step 402, the current shape of a catheter of a surgical instrument or another type of sensed device is acquired using one or more sensors of the sensor system. At step 404, a sampling of points along the shaped catheter relative to a sampling of points along the static model is matched for a best-fit. In greater detail, this best-fit matching technique may, in one example embodiment, include a) finding N links L that are closest to the tip of the catheter; b) for each of the N links L, computing the unique subset of links that form a path from that link to the base of the bronchial structure; c) for each of the N subsets, computing the closest points on the bronchial passageway to each of the sampled points along the catheter shape; d) computing a distance score for each of the N options as a function of the distances of the sampled points to the corresponding closest points in the bronchial passageway; and choosing the best option from the N options based on the lowest combined distance score. Thus, the most likely candidate passageway (or combination of anatomical links) is chosen based on a comparison of the curvature of the catheter and the curvature of the different passageways. Optionally, a plurality of candidate models may be determined.

At step 406, a set of deformation forces for the selected best fit (e.g., the selected passageway) model(s) are calculated. For each of the sampled points along the catheter shape, a force is defined as the vector between the position of the point and the position of the closest point on the bronchial passageway. As mentioned above, the catheter generally will include distinct sections having different physical properties, and the algorithm individually evaluates the forces applied by each distinct section based on its particular physical properties relative to its location within the patient anatomy (e.g., in real time). For example, the forces applied by a distal active section (e.g., the section 307 in FIG. 7C) may be greater and more deformative on the surrounding tissues than an inactive or more flexible section of the catheter (e.g., the section 306 in FIG. 7C). Thus, device-aware calculations are performed to accurately evaluate the deformation forces applied by different parts of the catheter.

At step 408, a set of restorative forces are computed that correspond to the forces that bias the bronchial passageway toward its original shape. These restorative forces are defined between sampled point on the deformed bronchial passageway links and corresponding points on the undeformed links. These restorative forces may depend upon a variety of factors, including by way of non-limiting example, the type of tissue, the fluid/air content of the tissue, the neighboring or supporting tissue, the mass of the tissue, the elasticity of the tissue, and the density of the tissue. Optionally, a subset of the restorative forces known as maintenance forces may be computed that correspond to the forces that bias the local shape to the undeformed local shape. These maintenance forces can be defined, for example, as joint torques acting between each pair of connected links with torque equal and opposite to the deformation angle at that connection. The total set of forces acting on the branched structure of bronchial passageways is computed as a weighted sum of the sets of deforming and restorative forces.

Different weight or weighting factors may be determined by a user or preset by the control system 116 in a way that results in the most realistic behavior, for example based on the known physical properties of the distinct sections of the catheter and the measured mechanical properties of the anatomy. The tissue's elastostatic properties can also be pre-estimated in multi-dimensional diagnostic images (e.g., 3D or 4D CT) possibly also involving real patient image databases for intensity to elasticity calibration. Since the CT imaging modality captures relative tissue density, a mapping between the image intensities and a tissue site's elastic properties can be pre-computed. During run time, tissue deformation under forces of known magnitude and direction for each distinct section of the catheter can be computed to reflect more physically accurate tissue behavior.

At step 410, one or more candidate deformation models of the bronchial passageways are created by adjusting each joint between the bronchial passageway links by an amount proportional to the total applied force and/or torque at the joint. Thus, the deformation model is created based upon both deformation forces associated with the physical properties of the distinct catheter sections and the restorative forces associated with the physical characteristics of the tissue affected by these catheter sections to refine the initial best-fit passageway selection(s). The candidate deformation models are compared to the current shape of the instrument body to determine which passageway best matches with the current shape of the instrument body. Alternatively, the candidate passageways are modeled to match the catheter shape and an evaluation is performed to determine which of the deformed models matching the catheter shape are most likely based upon the known deforming and restorative forces.

At step 412, a composite image of the deformed model and the catheter is generated to accurately depict the location of the catheter within the branched structure of the bronchial passageways. Additionally, with a tip of the catheter registered to the correct link in the deformed model, a correct virtual navigation view can be retrieved from the preoperatively stored images. The process may be repeated from step 402 until the catheter reaches its desired target within the bronchial structure.

Figure 10:
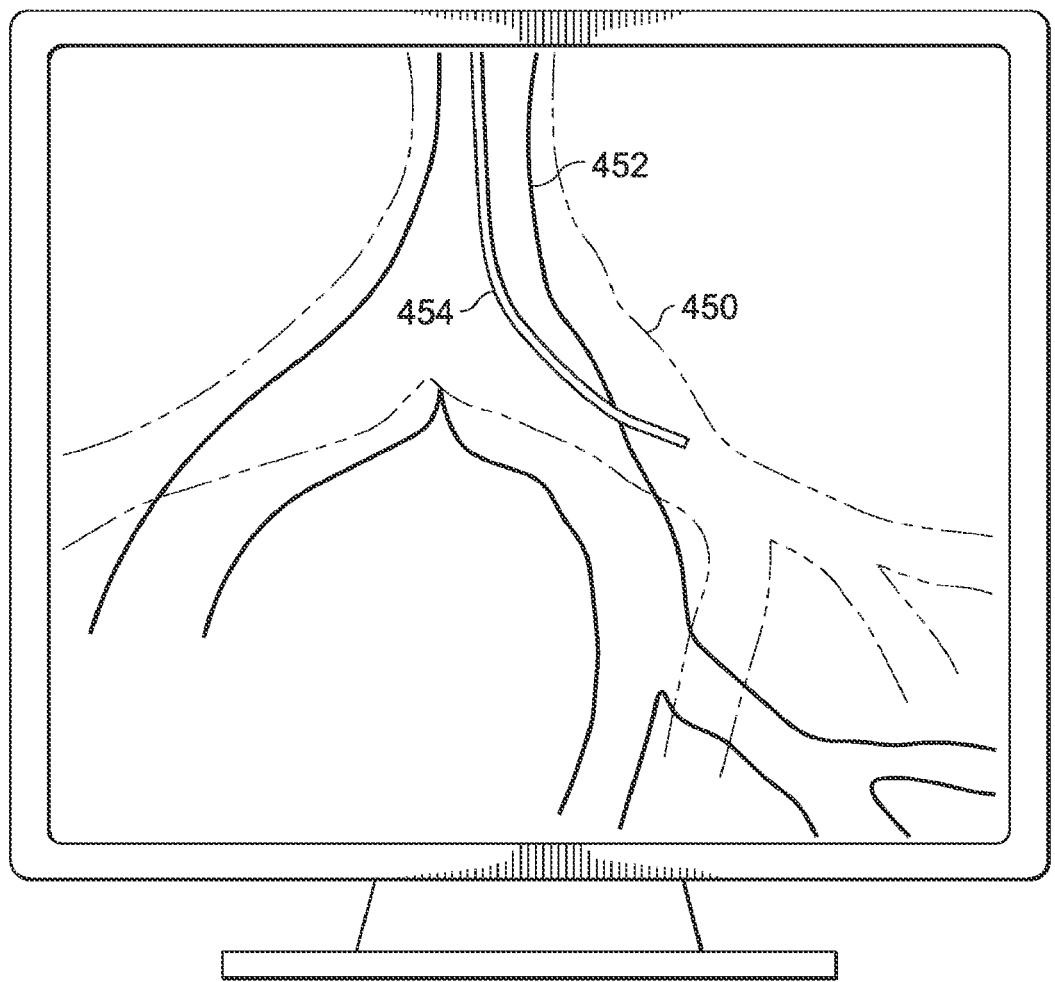
FIG. 10 is an illustration of a model of a bronchial passageway of a lung in states of expiration and inspiration.

In another embodiment, the non-static nature of the branched bronchial structure can be shown in an inspiration model of the bronchial structure that corresponds to an inhalation state of the bronchial structure and an expiration model that corresponds to an exhalation state of the bronchial structure. With reference to FIGS. 9 and 10, the pose, position, or orientation of a catheter already adjusted based upon a sensor system can be further refined or warped to the shape of a bronchial passageway as the passageway adjusts between a state of inspiration and expiration and vice versa. FIG. 9 depicts an inspiration model 450 and an expiration model 452. A catheter 454 is initially located based upon the sensor system but is adjusted to remain within the image of the bronchial passageways as they move between states of inspiration and expiration.

FIG. 10 is a flow chart 460 describing a method for adjusting the catheter based on states of inspiration and expiration. At step 462, the current shape of the catheter is acquired. At step 464, the catheter shape is matched to the shape of the bronchial passageway in a state of inspiration. At step 466, the catheter shape is matched to the shape of the bronchial passageway in a state of expiration. In a composite image of the bronchial passageways and the catheter, the image of the catheter is maintained within the bronchial passageways for each state of expiration and inspiration. The process may be repeated until the catheter reaches its desired target within the bronchial structure. In alternative embodiments, the process may be used to correct images for any instrument located within any moving anatomical structure, and in particular an anatomic structure, such as the heart or lungs, that repeatedly alternates between known states. For example, the moving anatomical structure may be a heart alternating between diastole and systole phases of the cardiac cycle.

Figure 11:
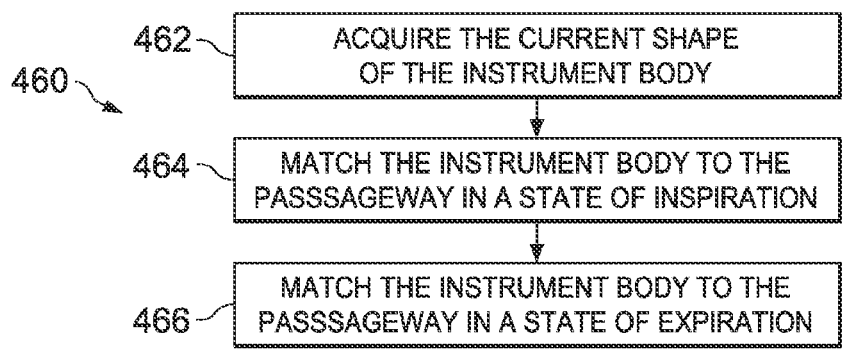
FIG. 11 is a flowchart illustrating a method of deforming a model of the bronchial passageway for states of inspiration and expiration.

In alternative embodiments, the instruments or the anatomic passageways may be modeled using three dimensional shape histograms to perform similarity searching. For example, a metric may be developed to measure similarity between two three-dimensional curves. With reference to FIG. 11, a curve 500 corresponds to a measured device path through a reference anatomy and a curve 502 corresponds to an actual anatomic passageway. For each point $P_i$ on these curves, the following parameters may be defined: a) local gradient, b) local curvature, c) radial angular displacement with respect to an endpoint connector, d) radial distance with respect to an endpoint connector, e) radial angular/displacements with respect to a third reference axis 504.

As shown in FIG. 12, a histogram 505 may be created from each of the above parameters. The histograms are matched directly to create a metric for each curve similarity.

In another embodiment, an arbitrarily shaped point set is snapped to another point set using a metric to measure the quality of the match. With reference to FIG. 13, two point sets $P_T$ and $P_S$ are provided. Starting with $P_S$, a similarity measure $|S_{S \to T}|$ is computed. The similarity measure is a one dimensional histogram indexed on distance from a reference point. The value of a tangent vector at the reference point is stored with respect to a reference vector. An optimizer is used to optimize the degrees of freedom on a transform to maximize the similarity measure at an instant between $P_S$ and $P_T$.

Alternative systems and methods for registering an image of at least a portion of a flexible instrument to an image of an anatomical system are disclosed in U.S. patent application Ser. No. 13/893,040, entitled "Systems and Methods for Registration of a Medical Device Using a Reduced Search Space" and in U.S. patent application Ser. No. 13/892,924, entitled "Systems and Methods for Registration of a Medical Device Using Rapid Pose Search," both of which are incorporated by reference herein in their entirety. Aspects of theses incorporated by reference systems and methods may be used together with the above disclosed systems and methods to provide alternative methods of accurately registering an image of at least a portion of a flexible instrument to an image of an anatomical system.

Although the registration systems and methods have been described herein with respect to teleoperated or hand operated surgical systems, these registration systems and methods will find application in a variety of medical and non-medical instruments in which accurate instrument image registration is otherwise too time consuming or computer processing intensive.

Although the systems and methods of this disclosure have been illustrated for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-surgical applications.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will he appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical system comprising:
  a flexible device configured to be positioned at least partially within an anatomical passageway of a plurality of anatomical passageways within a patient anatomy; and
  a memory device including computer executable instructions, the computer executable instructions for performing operations comprising:
    determining a deformation force exerted by a section of the flexible device; and
    registering a model of a candidate anatomical passageway of the plurality of anatomical passageways to a model of the flexible device based on:
      a shape of the flexible device; and
      the deformation force exerted by the section of the flexible device.

2. The medical system of claim 1, wherein the computer executable instructions further comprise instructions for identifying the candidate anatomical passageway in a model of the patient anatomy.

3. The medical system of claim 2, wherein the model of the patient anatomy comprises an undeformed model of the patient anatomy including a model of the plurality of anatomical passageways.

4. The medical system of claim 2, wherein the instructions for identifying the candidate anatomical passageway comprise instructions for matching a plurality of points of the model of the candidate anatomical passageway to a plurality of points of the model of the flexible device, the model of the flexible device based on the shape of the flexible device.

5. The medical system of claim 1, wherein the instructions for identifying the candidate anatomical passageway comprise instructions for comparing the shape of the flexible device to a shape of a model of each anatomical passageway of the plurality of anatomical passageways.

6. The medical system of claim 5, wherein the instructions for identifying the candidate anatomical passageway comprise instructions for eliminating at least one other anatomical passageway of the plurality of anatomical passageways from consideration based on the comparison of the shape of the flexible device to the shape of the model of each anatomical passageway of the plurality of anatomical passageways.

7. The medical system of claim 1, wherein the section of the flexible device comprises a distal section of the flexible device.

8. The medical system of claim 1, wherein the section of the flexible device comprises an actively controllable section.

9. The medical system of claim 8, wherein the actively controllable section comprises an actively controllable stiffness.

10. The medical system of claim 1, wherein the instructions for determining the deformation force comprise instructions for determining a stiffness of the section of the flexible device, the section of the flexible device comprising an actively controllable stiffness.

11. The medical system of claim 1, wherein the section of the flexible device comprises an actively controllable stiffness, and wherein the flexible device includes:
    a second section comprising a second stiffness; and
    a third section comprising a third stiffness, the third stiffness being greater than the second stiffness, and the actively controllable stiffness being greater than the third stiffness.

12. The medical system of claim 1, wherein the computer executable instructions further comprise instructions for determining the shape of the flexible device based on information from a shape sensor of the flexible device.

13. The medical system of claim 1, wherein the computer executable instructions further comprise instructions for generating a composite model of the patient anatomy based on the registering, and wherein the composite model includes the model of the flexible device positioned within the model of the candidate anatomical passageway.

14. The medical system of claim 1, wherein the computer executable instructions further comprise instructions for determining a restorative force corresponding to the deformation force exerted by the section of the flexible device, and wherein the instructions for registering the model of the candidate anatomical passageway of the plurality of anatomical passageways to the model of the flexible device is further based on the restorative force.

15. A medical system comprising:
    a flexible device configured to be positioned at least partially within an anatomical passageway of a plurality of anatomical passageways within a patient anatomy; and
    a memory device including computer executable instructions, the computer executable instructions for performing operations comprising:
        determining a deformation force exerted by an actively controllable section of the flexible device; and
        registering a model of a candidate anatomical passageway of the plurality of anatomical passageways to a model of the flexible device based on:
            a shape of the flexible device; and
            the deformation force exerted by the actively controllable section of the flexible device.

16. The medical system of claim 15, wherein the computer executable instructions further comprise instructions for identifying the candidate anatomical passageway in a model of the patient anatomy by matching a plurality of points of the model of the candidate anatomical passageway to a plurality of points of the model of the flexible device.

17. The medical system of claim 16, wherein the model of the patient anatomy comprises an undeformed model of the patient anatomy including a model of the plurality of anatomical passageways.

18. The medical system of claim 16, wherein identifying the candidate anatomical passageway comprises comparing the shape of the flexible device to a shape of a model of each anatomical passageway of the plurality of anatomical passageways.

19. The medical system of claim 15, wherein the computer executable instructions further comprise instructions for determining a restorative force corresponding to the deformation force exerted by the actively controllable section of the flexible device, wherein the registering the model of the candidate anatomical passageway of the plurality of anatomical passageways to the model of the flexible device is further based on the restorative force.

20. The medical system of claim 15, wherein the actively controllable section is positioned at a distal portion of the flexible device.

* * * * *